(12) United States Patent
Tian et al.

(10) Patent No.: US 11,268,944 B2
(45) Date of Patent: Mar. 8, 2022

(54) METHOD FOR DETERMINING GAS SATURATION OF TIGHT RESERVOIR

(71) Applicant: PetroChina Company Limited, Beijing (CN)

(72) Inventors: Hua Tian, Beijing (CN); Caineng Zou, Beijing (CN); Shuichang Zhang, Beijing (CN); Shaobo Liu, Beijing (CN); Xuesong Lu, Beijing (CN); Zhichao Yu, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 189 days.

(21) Appl. No.: 16/776,773

(22) Filed: Jan. 30, 2020

(65) Prior Publication Data

US 2020/0249216 A1    Aug. 6, 2020

(30) Foreign Application Priority Data

Feb. 1, 2019   (CN) .......................... 201910104816.1

(51) Int. Cl.
   *G01N 33/24*     (2006.01)
   *E21B 49/02*     (2006.01)
   *G01N 15/08*     (2006.01)

(52) U.S. Cl.
   CPC .......... *G01N 33/241* (2013.01); *E21B 49/02* (2013.01); *G01N 15/0886* (2013.01)

(58) Field of Classification Search
   CPC .. G01N 33/241; G01N 15/0886; E21B 49/02; A61B 34/30; G01V 3/14; G01V 11/00
   See application file for complete search history.

(56) References Cited

U.S. PATENT DOCUMENTS 9,757,203 B2 *  9/2017  Hourtash ............... A61B 34/30
10,495,774 B2 * 12/2019  Kleinberg .......... G01N 15/0886
(Continued)

FOREIGN PATENT DOCUMENTS

CN       101806215 A      8/2010
CN       103513270 A      1/2014
(Continued)

OTHER PUBLICATIONS

Marcos F.P. Moreira "Total Liquid Saturation in Gas-Liquid Cocurrent Downflow and Upflow through packed Beds and Analysis of Correlations for Predicting the total Liquid Saturation" (Year: 2004).*

(Continued)

*Primary Examiner* — Regis J Betsch
*Assistant Examiner* — Kaleria Knox
(74) *Attorney, Agent, or Firm* — The Dobrusin Law Firm, P.C.; Bryan S. Lemanski

(57) ABSTRACT

The present invention a method for determining the gas saturation of a tight reservoir. The method comprises the steps of: determining the pore size distribution of the tight reservoir rock sample, and calculating the free water saturation; calculating the water-membrane water saturation; calculating the corner water saturation; calculating the gas saturation of the tight reservoir rock sample according to the following equation:

$$S_g = 100 - S_w$$

wherein $S_w$ is the water saturation in %; $S_w$ is the sum of the free water saturation, the water saturation and the corner water saturation; $S_g$ is the gas saturation in %. The method for determining the gas saturation of a tight reservoir uses model calculations, which avoids errors in the determination results of the gas saturation caused (Continued)

by water volatilization, surface adsorption, and observation of water flow during experiments.

9 Claims, 4 Drawing Sheets

(56) References Cited

U.S. PATENT DOCUMENTS

| | | | |
|---|---|---|---|
| 2013/0103319 A1* | 4/2013 | Buiting | G01V 11/00 |
| | | | 702/12 |
| 2015/0198036 A1* | 7/2015 | Klein | G01V 3/14 |
| | | | 702/12 |

FOREIGN PATENT DOCUMENTS

| | | |
|---|---|---|
| CN | 104358565 A | 2/2015 |
| CN | 105445441 A | 3/2016 |
| WO | 2014/077833 A1 | 5/2014 |

OTHER PUBLICATIONS

Chinese Search Report, Application No. 201910104816.1, dated Dec. 11, 2018.
Study on critical conditions of secondary mobile water flow in low-permeability gas reservoirs, Natural gas exploration and development, vol. 34, No. 1, Jan. 2011.
A new method of quantitative characterization of condensate critical flow saturation, Journal of Shenzhen University Science and Engineering, vol. 34, No. 1, Jan. 2017.

* cited by examiner

METHOD FOR DETERMINING GAS SATURATION OF TIGHT RESERVOIR

CROSS-REFERENCE TO RELATED APPLICATIONS

This application claims priority to Chinese Patent Application No. 201910104816.1, filed on Feb. 1, 2019, which is hereby incorporated by reference in its entirety.

TECHNICAL FIELD

The present invention relates to a method for determining the gas saturation of a tight reservoir, which belongs to the technical field of oil and gas determination.

BACKGROUND

The natural gas content of underground rocks is usually calculated using a volume method, which requires four key parameters: gas saturation, porosity, rock density, and formation factor. Among them, the gas saturation varies widely. At present, the gas saturation of a tight reservoirs is measured by natural gas injection in a lab. Natural gas is injected into the rock with saturated water while maintaining a certain filling pressure. When it is observed that the water no longer flows out of the outlet, the rock core is taken out, followed by weighing the reduced mass of the rock core before and after the experiment to calculate the injected gas volume, and its ratio to the pore volume is the gas saturation. By changing different injection pressures, the gas saturation under different filling pressure conditions can be obtained.

Tight reservoirs have low porosity, are easily affected by experimental conditions, and have increased errors. Specifically, this method has the following disadvantages: 1. during the experiment, the liquid measurement is not accurate, the tight reservoir itself has low porosity, and the water content of the rock is small, which is easily affected; if the processes of sample loading, sampling and weighing take a long time, the water in the rock is volatile, resulting in a low water content; the adsorption of water on the surface of the rock tends to increase the water content; 2. the end condition of the experiment is to observe no more water flowing out of the outlet, the water existing in the pipeline cannot be observed, and the filled water cannot be seen in the pipeline, leading to the end of the experiment in advance, and a smaller gas saturation; 3. to determine the gas saturation at multiple pressure points, one need to take a sample to determine the gas saturation at each pressure point, then saturate water again and determine the saturation corresponding to the next pressure point; the sample is repeated for a long time and the process is tedious; 4. repetitive filling of rocks and saturating water can easily change the pore structure of rocks, such as resulting in micro-fractures; 5. repetitive filling of wet rocks and saturating water can easily change the wettability of rocks, for example, if becoming from hydrophilic to hydrophobic, it is easy to form dominant channels, resulting in incomplete gas filling; 6. it is difficult to fully achieve the temperature and pressure conditions in the experiment, the fluid pressure is less than 70 MPa and the temperature is less than 200° C.; 7. only a single value for total gas saturation can be determined.

SUMMARY

In order to solve the above technical problems, an object of the present invention is to provide a method for determining the gas saturation of a tight reservoir, which can overcome the disadvantages of the methods in the prior art, such as complexity, inaccurate results, difficulty in meeting underground high temperature and high-pressure geological conditions, etc.

In order to achieve the above object, the present invention provides a method for determining the gas saturation of a tight reservoir, comprising:

a free water saturation calculation step: determining the pore size distribution of the tight reservoir rock sample, and calculating the free water saturation of the tight reservoir rock sample from the pore size distribution;

a water-membrane water saturation calculation step: calculating the water-membrane water saturation of the tight reservoir rock sample;

a corner water saturation calculation step: calculating the corner water saturation of the tight reservoir rock sample;

a gas saturation calculation step: calculating the gas saturation of the tight reservoir rock sample according to the following equation:

$$S_g = 100 - S_w$$

wherein $S_w$ is the water saturation in %; the water saturation is the sum of the free water saturation, the water-membrane water saturation and the corner water saturation; $S_g$ is the gas saturation in %.

The determination method provided in the present invention is based on assuming that the reservoir rock contains only two fluids, formation water and natural gas, and the gas saturation is directly affected by the rock water saturation; if the reservoir water saturation is obtained, the gas saturation can be obtained; the size and stacking relationship of the rock-forming mineral particles determine the geometry and spatial distribution of the fluid storage space; the formation water exists in rocks in three main forms: (1) free water: pore water that cannot be expelled by natural gas, occupying small pore throats that cannot be filled, and its saturation is affected by natural gas filling pressure and pore throat capillary force; (2) water-membrane water: adsorbed on the pore wall in the form of a thin membrane, its saturation is related to the surface area of the pore wall and the thickness of the water-membrane; (3) corner water: existing in the corners that are difficult to displace among the particles, and its saturation is affected by the size and the contact relationship of the rock particles.

In the above method, the pore size distribution of the tight reservoir rock sample can be determined by mercury porosimetry, nuclear magnetic resonance method, etc., but it is not limited to the above two methods. The basic principle of rock pore diameter measurement using the mercury porosimetry is that mercury does not wet the rock surface and is a non-wetting phase, and the air in the rock pores is a wetting phase. The process of mercury injection into rock pores is to displace the wetting phase with a non-wetting phase. Due to the effect of the capillary pressure at the pore throat, mercury cannot enter the pores when the pressure is low. Only when the injection pressure exceeds the capillary pressure, mercury can enter the pore throat of the rock sample. The injection pressure at this time is the capillary pressure. The capillary radius corresponding to the capillary pressure is equivalent to the pore throat radius, and the volume of mercury entering the pores is the pore volume. The injection pressure is increased such that mercury enters the pores controlled by a smaller throat. In this manner, by continuously increasing the injection pressure, the relationship between the injection pressure, that is, the capillary pressure, and the pore volume can be obtained. The gas saturation of the wetting phase can be calculated from the volume of mercury injected and the pore volume of the tight reservoir rock sample, and then the curve of the pore size distribution of different pore throat radius ranges and the capillary pressure can be obtained. In the free water saturation calculation step, the data of the pore size distribution includes data of pore spaces corresponding to different pore throat radii.

In the above method, preferably, in the free water saturation calculation step, the data of pore spaces corresponding to different pore throat radii includes the pore throat radii corresponding to the pore spaces with different radii and the percentages of pore volumes occupied by the pore spaces with different radii.

In the above method, preferably, in the free water saturation calculation step, the pore size distribution of the tight reservoir rock sample is determined by the mercury porosimetry as follows:

injecting mercury into rock pores to displace air in rock pores;

when the injection pressure exceeds the capillary pressure, mercury entering the pore throat of the rock sample, and at this time, the injection pressure being the capillary pressure, the capillary radius corresponding to the pressure is equivalent to the pore throat radius, and the volume of mercury entering the pores being the pore volume;

increasing the injection pressure such that mercury enters the pores controlled by a smaller throat, to obtain the pore throat radius and the pore volume corresponding to the smaller throat; and repeatedly increasing the injection pressure to obtain the pore throat radii and the pore volumes corresponding to different throats.

In the above method, since the surface tension of the fluid system in the laboratory is different from that of the oil reservoir system, it is necessary to convert the laboratory's capillary pressure data into the oil reservoir capillary pressure. Assuming that the "J" function is a parameter of rock characteristics and does not change from the laboratory to the gas reservoir, the mercury porosimetry curve can be converted into the relationship between the water saturation and the filling pressure (e.g., FIG. 3), according to the actual gas reservoir conditions. In the free water saturation calculation step, the free water saturation of the tight reservoir rock sample is calculated from the pore size distribution as follows:

(1) obtaining the relationship between the injection pressure and the pore volume from the pore throat radii and the pore volumes corresponding to different throats in the tight reservoir rock sample;

$$P_{mercury-air} = \frac{2\sigma_{mercury-air} \cos\theta_{mercury-air}}{r}$$

wherein $P_{mercury-air}$ is the capillary pressure in $10^6$ Pa; $\sigma_{mercury-air}$ is the fluid interfacial tension between mercury and air in mN/m; $\theta_{mercury-air}$ is the wet contact angle between mercury and air in °; r is the capillary radius in $10^{-9}$ m; in the mercury porosimetry, $\sigma_{mercury-air}$=480 mN/M, $\theta_{mercury-air}$=140°;

(2) calculating the gas saturation from the volume of mercury injected and the pore volume of the tight reservoir rock sample, and then obtaining the curve of the pore size distribution of different pore throat radius ranges and the capillary pressure:

$$P_{filling} = \frac{2\sigma_{gas-water} \cos\theta_{gas-water}}{r}$$

$\sigma_{gas-water}$ is the interfacial tension in mN/m; preferably, the gas-water interfacial tension $G_{gas-water}$=20 mN/m;

$\theta_{gas-water}$ is the gas-water contact angle; preferably, $\theta$ is 0, and cos $\theta$=1;

$P_{filling}$ is the gas-water filling pressure in MPa;

r is the capillary radius in $10^{-9}$ m;

(3) converting the curve of the pore size distribution of different pore throat radius ranges and the capillary pressure into the relationship curve of free water saturation and capillary pressure; obtaining the free water saturation from the filling pressure, that is, calculating the corresponding pore throat radius from the filling pressure, and summing the pore volumes larger than this radius, the percentage of this sum to the total pore volumes being the free water saturation.

In the above method, preferably, the water-membrane water saturation calculation step is performed as follows:

(1) it is inappropriate for the irreducible water saturation method to regard the thickness of the water-membrane in the reservoir as a constant value, and the thickness of the water-membrane in the reservoir cannot be the lower limit of the available pore throat radius in the reservoir (see FIG. 1). Using DIvo theory, the calculation equation of the water-membrane thickness is given, that is, calculating the water-membrane thicknesses in the pore spaces corresponding to different pore throat radii according to the following equation:

$$h = \left(\frac{a \cdot r}{\sigma}\right)^{1/3}$$

wherein, a is a constant; the more hydrophilic the reservoir is, the greater is its value, which is preferably 1.18× $10^{-7}$; h is the water-membrane thickness in μm; σ is the fluid interfacial tension in mN/m; r is the pore throat radius in $10^{-9}$ m;

(2) as seen from the above, a layer of water-membrane will leave after uniform oil and water displacement in a single pipe; the water-membrane is an integral part of the irreducible water; the thickness of the water-membrane will become thinner as the surface tension increases, and will gradually increase as the pore size becomes larger; the volume occupied by the water-membrane is compared with the capillary volume to calculate the irreducible water saturation of the water-membrane, that is, calculating the water-membrane saturation according to the following equation:

$$S_{wmi} = \frac{V_{water-membrane}}{V_{sum}} = \frac{r^2 - (r-h)^2}{r^2}$$

wherein $S_{wmi}$ is water-membrane water saturation of the pore space corresponding to the i-th pore throat radius;

r is the pore throat radius which corresponds to the pore space corresponding to the i-th pore throat radius;

h is the water-membrane thickness which corresponds to the pore space corresponding to the i-th pore throat radius.

In the above method, the corner water saturation of the reservoir is affected by the shape of the pores. In ideal cases, such as regular arrangement of spherical particles, triangular arrangement of spherical particles, regular triangle pores, square pores, regular hexagonal pores, the water saturation values can be calculated. For specific reservoirs, a simpler method can be used for the calculation of corner water saturation by observing the pore structure of the reservoir and directly determining the corner water saturation, or by counting the proportions of different types of pore structure, and determining the corner water saturation by weighted average. Preferably, the corner water saturation calculation step is performed by one of:

(1) observing the pore structure of the reservoir and directly determining the corner water saturation;

(2) counting the proportions of corner water corresponding to different types of pore structure, and determining the corner water saturation by weighted average;

(3) the pressure of the water-membrane on the surface of the particles is unstable, and it will gather towards the corner. In the particle model, most of the irreducible water is distributed in the corners between the particles (see FIG. 2), forming corner water. The water saturation equation of the particle model is as follows, and the corner water saturation can be calculated according to the following equation:

$$S_{wyi} = \frac{A_3}{A_2+A_3} = \frac{4}{4-\pi}\left[\sqrt{\left(\frac{r}{R}\right)^2+2\frac{r}{R}} - \arccos\left(\frac{R}{R+r}\right) - \left(\frac{r}{R}\right)^2 \arcsin\left(\frac{R}{R+r}\right)\right]$$

wherein, A2 is the circular cross-sectional area of the air-water interface;

A3 is the cross-sectional area of the corner water;

r is the arc radius of air-water interface, that is, the pore throat radius, $$r = \frac{2\sigma}{p_{filling}}$$

in $10^{-9}$ m;

R is the particle radius of the tight reservoir rock sample in $10^{-9}$ m;

$S_{wyi}$ is water saturation of the pore space corresponding to the i-th pore throat radius;

$P_{filling}$ is the filling pressure in MPa;

σ is the fluid interfacial tension in mN/m.

In the above method, preferably, the gas saturation calculation step is performed as follows:

(1) calculating the water saturation according to the following equation:

$$S_w = \sum_{i=1}^{n}\lambda_i(S_{wyi}+S_{wmi}) + S_{wz}$$

wherein $S_w$ is the water saturation;

$\lambda_i$ is the percentage of pore volume occupied by the pore space corresponding to the i-th pore throat radius;

$S_{wyi}$ is the corner water saturation in the pore space corresponding to the i-th pore throat radius;

$S_{wmi}$ is the water-membrane water saturation in the pore space corresponding to the i-th pore throat radius;

$S_{wz}$ is the free water saturation, that is, the proportion of pore volume occupied by free water pore space;

(2) calculating the gas saturation of the tight reservoir rock sample according to the following equation:

$$S_g = 100 - S_w$$

wherein $S_w$ is water saturation in %; the water saturation is the sum of the free water saturation, the water-membrane water saturation and the corner water saturation;

$S_g$ is the gas saturation in %.

According to a specific embodiment of the present invention, preferably, the method provided in the present invention comprises the following steps:

a free water saturation calculation step:

determining the pore size distribution of the tight reservoir rock sample by mercury porosimetry; when the injection pressure exceeds the capillary pressure, mercury entering the pore throat of the rock sample, and at this time, the injection pressure being the capillary pressure, the capillary radius corresponding to the capillary pressure being equivalent to the pore throat radius, and the volume of mercury entering the pores being the pore volume;

increasing the injection pressure such that mercury enters the pores controlled by a smaller throat, to obtain the corresponding pore throat radius and pore volume;

continuously increasing the injection pressure to obtain the relationship between the injection pressure, that is, the capillary pressure, and the pore volume;

calculating the gas saturation from the volume of mercury injected and the pore volume of the tight reservoir rock sample, and then obtaining the curve of the pore size distribution of different pore throat radius ranges and the capillary pressure;

converting the pore size distribution data of the tight reservoir rock sample into the capillary pressure of oil reservoir; and converting the mercury porosimetry curve into the relationship of water saturation according to the displacement pressure difference, in consideration of the interfacial tension and the contact angle under the conditions of actual gas reservoir temperature and pressure:

$$P_{filling} = \frac{2\sigma_{gas-water}\cos\theta_{gas-water}}{r}$$

converting the curve of pore size distribution data and capillary pressure of the tight reservoir rock sample into the curve of free water saturation and capillary pressure, to obtain the filling pressure, so as to obtain the free water saturation; that is, calculating the corresponding pore throat radius from the filling pressure, and summing the pore volumes larger than this radius, the percentage of this sum to the total pore volumes being the free water saturation.

$\sigma_{gas-water}$ is the interfacial tension in mN/m; preferably, the gas-water interfacial tension $\sigma_{gas-water}$=20 mN/m;

$\theta_{gas-water}$ is the gas-water contact angle; preferably, θ is 0, and cos θ=1;

$P_{filling}$ is the filling pressure in MPa;

r is the capillary radius in $10^{-9}$ m;

a water-membrane water saturation calculation step:
calculating the water-membrane thicknesses in the pore spaces corresponding to different pore throat radii according to the following equation:

$$h = \left(\frac{a \cdot r}{\sigma}\right)^{1/3}$$

wherein a is a constant; the more hydrophilic the reservoir is, the greater is its value, which is preferably $1.18 \times 10^{-7}$; h is the water-membrane thickness in μm; σ is the fluid interfacial tension in mN/m; r is the pore throat radius in $10^{-9}$ m;

calculating the water-membrane saturation according to the following equation:

$$S_{wmi} = \frac{V_{water-membrane}}{V_{sum}} = \frac{r^2 - (r-h)^2}{r^2}$$

wherein $S_{wmi}$ is the water-membrane water saturation of the pore space corresponding to the i-th pore throat radius;

r is the pore throat radius which corresponds to the pore space corresponding to the i-th pore throat radius;

h is the water-membrane thickness which corresponds to the pore space corresponding to the i-th pore throat radius;

a corner water saturation calculation step:
calculating the corner water saturation according to the following equation:

$$S_{wyi} = \frac{A_3}{A_2 + A_3} = \frac{4}{4-\pi}\left[\sqrt{\left(\frac{r}{R}\right)^2 + 2\frac{r}{R}} - \arccos\left(\frac{R}{R+r}\right) - \left(\frac{r}{R}\right)^2 \arcsin\left(\frac{R}{R+r}\right)\right]$$

wherein r is the arc radius of air-water interface, that is, the pore throat radius, $$r = \frac{2\sigma}{p_{filling}}$$

in $10^{-9}$ m;

R is the particle radius of the tight reservoir rock sample in $10^{-9}$ m;

$S_{wyi}$ is the water saturation of the pore space corresponding to the i-th pore throat radius;

$P_{filling}$ is the filling pressure in MPa;
σ is the fluid interfacial tension in mN/m;
a gas saturation calculation step:
calculating the water saturation according to the following equation:

$$S_w = \sum_{i=1}^{n} \lambda_i (S_{wyi} + S_{wmi}) + S_{wz}$$

wherein $S_w$ is the water saturation;
$\lambda_i$ is the percentage of pore volume occupied by the pore space corresponding to the i-th pore throat radius;
$S_{wyi}$ is the corner water saturation in the pore space corresponding to the i-th pore throat radius;

$S_{wmi}$ is the water-membrane water saturation in the pore space corresponding to the i-th pore throat radius;

$S_{wz}$ is the free water saturation, that is, the proportion of pore volume occupied by the free water pore space;

then calculating the gas saturation of the tight reservoir rock sample according to the following equation:

$$S_g = 100 - S_w$$

wherein $S_w$ is the water saturation in %; the water saturation is the sum of the free water saturation, the water-membrane water saturation and the corner water saturation; $S_g$ is the gas saturation in %.

The method for determining gas saturation of a tight reservoir provided in the present invention has the following beneficial effects:

1. using model calculations to avoid errors in the determination results of the gas saturation caused by water volatilization, surface adsorption, and observation of water flow during experiments;
2. avoiding the effect of repeated rock filling on the pore structure and wettability;
3. directly obtaining the gas saturation at multiple pressure points, which is simple and fast;
4. meeting the conditions of underground temperature and pressure, where the fluid pressure can be greater than 70 MPa, and the temperature can be greater than 200° C.;
5. separately obtaining the saturation and proportion of three kinds of water: free water, water-membrane and corner water;
6. not only determining the single value of total gas saturation, but also giving the gas saturation distribution at different pore sizes.

As compared with the existing method, the determination method of the present invention has shorter test time, requires less sample, has no requirements on the shape of the sample (either core plunger or rock cuttings), is safe and environmentally friendly, can use no mercury (e.g., Examples 2 and 3), and saves test gas. By subdividing the irreducible water saturation of the prior art into water-membrane water saturation and corner water saturation, the method of the present invention can overcome the disadvantages of the methods in prior art, such as complexity, inaccurate results caused by insufficient filling time, difficulty in meeting underground high temperature and high pressure geological conditions, etc, while it avoids errors in determination results of the gas saturation caused by water volatilization, surface adsorption, and observation of water flow during experiments.

DETAILED DESCRIPTION

Figure 1:
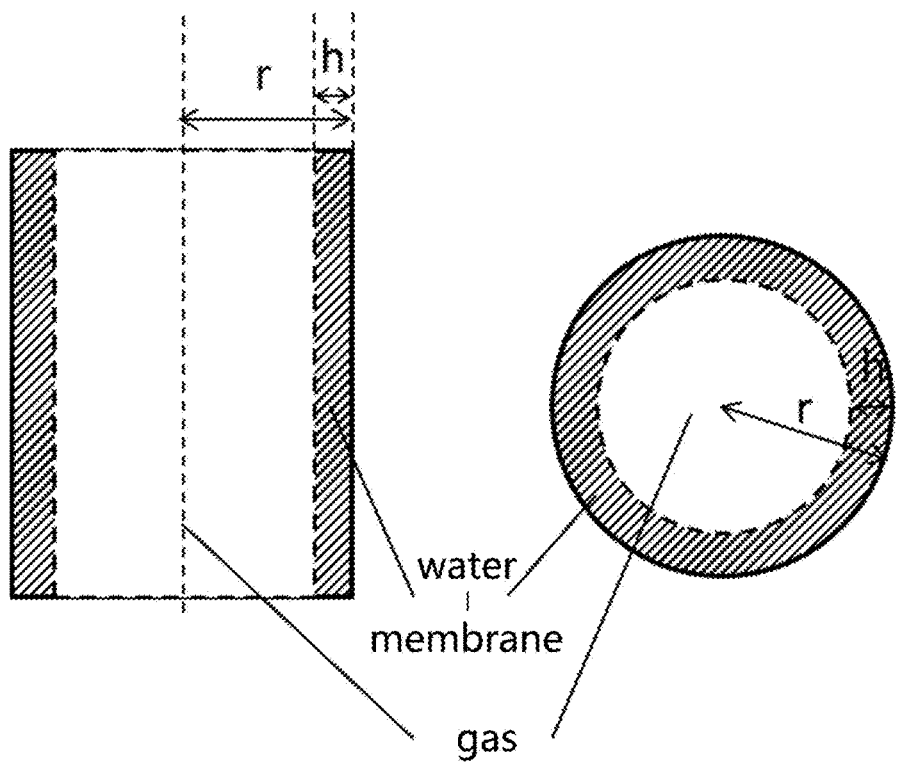
FIG. 1 is a schematic diagram of water-membrane water saturation calculation.

In order to have a clearer understanding of the technical features, objectives, and beneficial effects of the present invention, the technical solutions of the present invention will now be described below in detail, but cannot be understood as limiting the implementable scope of the present invention.

Example 1

This example provides a method for determining the gas saturation of a tight reservoir, which can theoretically be used for different types of rock samples. In this example, a Sandstone 1 sample is used for illustration. For different samples, input parameters are different, and the corresponding results will be different. The method includes the following steps.

The pore size distribution of the sample is measured using high-pressure mercury porosimetry, and the results are shown in Table 1.

TABLE 1

The pore size distribution of the Sandstone 1 sample

| No., i | Pore throat radius $r_i$, μm | $\lambda_i$, % |
|---|---|---|
| 1 | 2.931 | 0.00 |
| 2 | 1.909 | 5.22 |
| 3 | 1.228 | 12.77 |
| 4 | 0.952 | 6.83 |
| 5 | 0.621 | 8.90 |
| 6 | 0.399 | 7.30 |
| 7 | 0.256 | 7.35 |
| 8 | 0.206 | 3.37 |
| 9 | 0.134 | 6.73 |
| 10 | 0.089 | 6.32 |
| 11 | 0.056 | 6.71 |
| 12 | 0.037 | 5.12 |
| 13 | 0.024 | 5.41 |
| 14 | 0.015 | 4.96 |
| 15 | 0.012 | 2.40 |
| 16 | 0.010 | 2.17 |
| 17 | 0.008 | 2.15 |
| 18 | 0.007 | 2.24 |
| 19 | 0.005 | 1.69 |
| 20 | 0.004 | 1.50 |
| 21 | 0.004 | 0.84 |

(1) Free Water Saturation:

the pore size distribution data are converted to the capillary pressure of oil reservoir. The mercury porosimetry curve is converted into the relationship between water saturation and displacement pressure difference, in consideration of the interfacial tension, contact angle, and the like, under the conditions of actual gas reservoir temperature and pressure:

$$P_{filling} = \frac{2\sigma_{gas-water} \cos\theta_{gas-water}}{r}$$

The curve of pore size distribution data and capillary pressure measured in the laboratory is converted into the curve of free water saturation and capillary pressure, to obtain the filling pressure, and thus the free water saturation.

Figure 2:
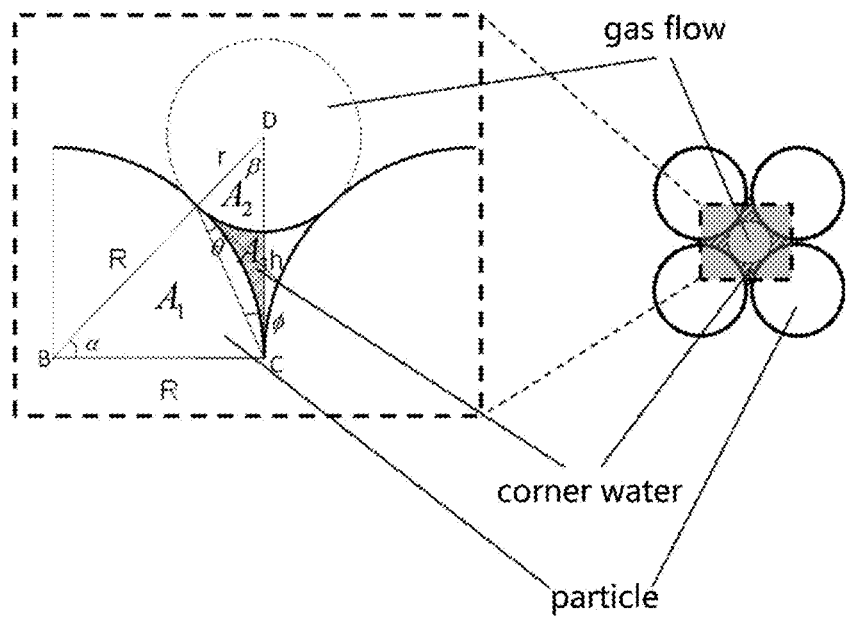
FIG. 2 is a schematic diagram of corner water calculation in a particle model.

$\sigma_{gas-water}$ is the interfacial tension in mN/m; in this example, the gas-water interfacial tension $\sigma_{gas-water}$=20 mN/m;

$\theta_{gas-water}$ is the gas-water contact angle, θ is 0, and thus cos θ=1;

$P_{filling}$ is the gas-water filling pressure in MPa;

r is the capillary radius in $10^{-9}$ m;

(2) Water-Membrane Water Saturation:

The water-membrane thicknesses in the pore spaces corresponding to different pore throat radii is calculated according to the following equation:

$$h_i = \left(\frac{1.18 \times 10^{-4} r_i}{\sigma}\right)^{1/3}$$

wherein $h_i$ is the water-membrane thickness which corresponds to the pore space corresponding to the i-th pore throat radius in μm; σ is the fluid interfacial tension in mN/m; $r_i$ is the pore throat radius which corresponds to the pore space corresponding to the i-th pore throat radius; in this example, i is 1-20, and specific data are shown in Table 1;

the water-membrane saturation is calculated according to the following equation:

$$S_{wmi} = \frac{V_{water film}}{V_{sum}} = \frac{r_i^2 - (r_i - h_i)^2}{r_i^2}$$

wherein $S_{wmi}$ is the water-membrane water saturation of the pore space corresponding to the i-th pore throat radius;

$r_i$ is the pore throat radius which corresponds to the pore space corresponding to the i-th pore throat radius; in this example, i is 1-20, and specific data are shown in Table 1;

$h_i$ is the water-membrane thickness which corresponds to the pore space corresponding to the i-th pore throat radius;

(3) Corner Water Saturation:

The corner water saturation is calculated according to the following equation (see FIG. 2):

$$S_{wyi} = \frac{A_3}{A_2 + A_3} = \frac{4}{4-\pi}\left[\sqrt{\left(\frac{r_i}{R_i}\right)^2 + 2\frac{r_i}{R_i}} - \arccos\left(\frac{R_i}{R_i + r_i}\right) - \left(\frac{r_i}{R_i}\right)^2 \arcsin\left(\frac{R_i}{R_i + r_i}\right)\right]$$

wherein $r_i$ is the arc radius of air-water interface, that is, the pore throat radius, $$r_i = \frac{2\sigma}{P_{filling\ i}}$$

in $10^{-9}$ m;

$R_i$ is the particle radius of the tight reservoir rock sample in $10^{-9}$ m;

$S_{wyi}$ is the water saturation of the pore space corresponding to the i-th pore throat radius;

$P_{filling\ i}$ is the filling pressure of the pore space corresponding to the i-th pore throat radius in MPa;

σ is the fluid interfacial tension in mN/m;

(4) Gas Saturation:

The water saturation is calculated according to the following equation:

$$S_w = \sum_{i=1}^{n} \lambda_i (S_{wyi} + S_{wmi}) + \lambda_z S_{wz}$$

wherein $S_w$ is the water saturation;

$\lambda_i$ is the percentage of pore volume occupied by the pore space corresponding to the i-th pore throat radius;

$\lambda_z$ is the proportion of pore volume occupied by free water pore space;

$S_{wyi}$ is the corner water saturation in the pore space corresponding to the i-th pore throat radius;

$S_{wmi}$ is the water-membrane water saturation in the pore space corresponding to the i-th pore throat radius;

$S_{wz}$ is the free water saturation, which has not been filled and is 100%.

Figure 3:
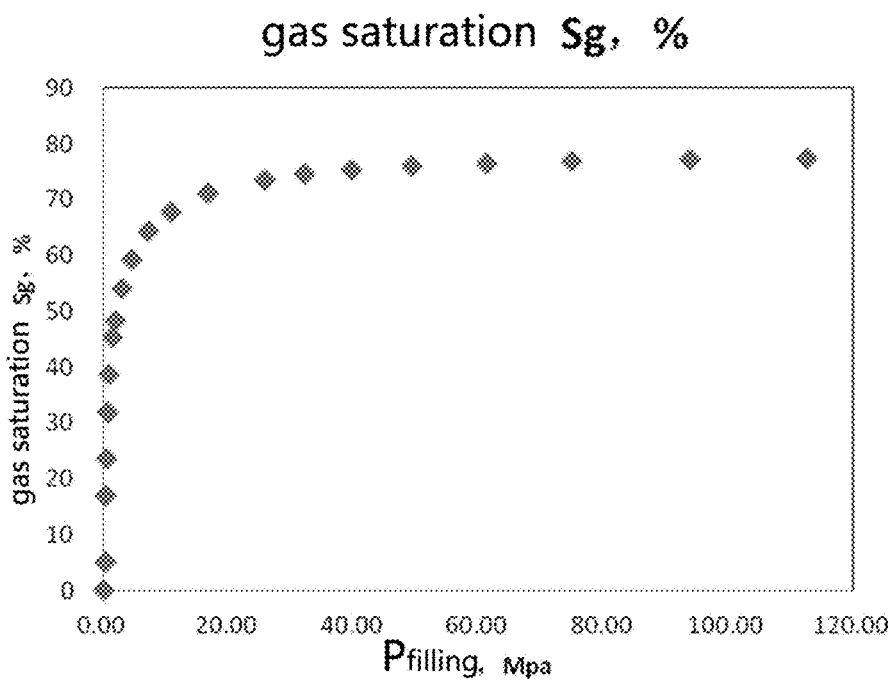
FIG. 3 is a relationship diagram between the filling pressure and the gas saturation in Example 1.
Figure 4:
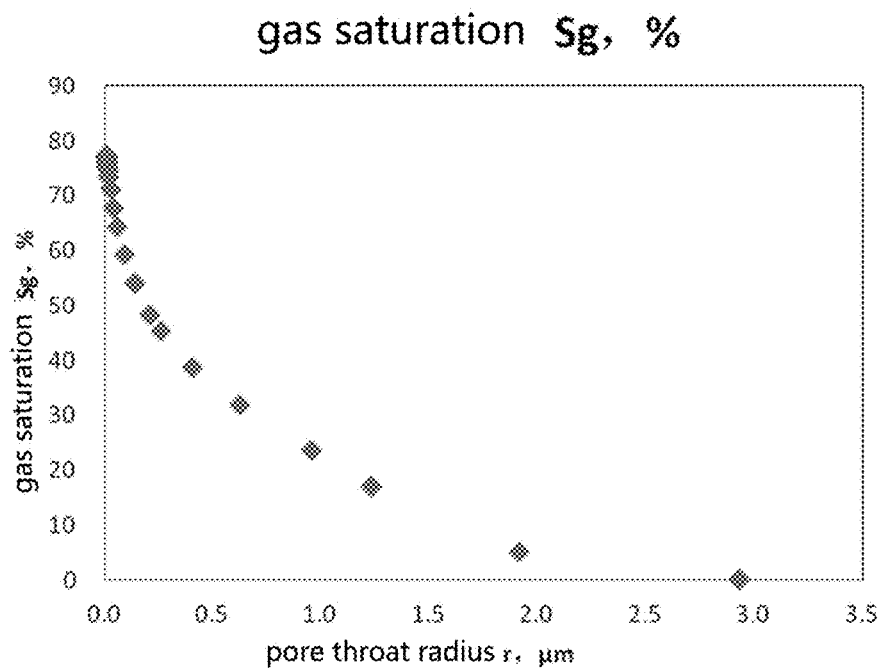
FIG. 4 is a relationship diagram between the filled pore throat radius and the gas saturation in Example 1.

The relationship between the filling pressure and the gas saturation is shown in FIG. 3, and the relationship between the filled pore throat radius and the gas saturation is shown in FIG. 4.

The gas saturation of the tight reservoir rock sample is then calculated according to the following equation:

$$S_g = 100 - S_w$$

wherein $S_w$ is the water saturation in %; the water saturation is the sum of the free water saturation, the water-membrane water saturation and the corner water saturation;

$S_g$ is the gas saturation in %.

The parameters of this example are shown in Table 2.

TABLE 2

Parameters of this example

| No., i | Pore throat radius r, μm | $\lambda_i$ % | $P_{filling}$ MPa | Swmi % | Water membrane thickness h, μm | Swyi % | Particle radius R μm | Swz % | Water saturation Sw % | Gas saturation Sg % |
|---|---|---|---|---|---|---|---|---|---|---|
| 1 | 2.931 | 0.00 | 0.14 | 0.00 | 0.026 | 0.00 | 7.08 | 100 | 100 | 0 |
| 2 | 1.909 | 5.22 | 0.21 | 0.12 | 0.022 | 0.94 | 4.61 | 95 | 95 | 5 |
| 3 | 1.228 | 12.77 | 0.33 | 0.40 | 0.019 | 2.29 | 2.97 | 82 | 83 | 17 |
| 4 | 0.952 | 6.83 | 0.42 | 0.25 | 0.018 | 1.23 | 2.30 | 75 | 76 | 24 |
| 5 | 0.621 | 8.90 | 0.64 | 0.44 | 0.015 | 1.60 | 1.50 | 66 | 68 | 32 |
| 6 | 0.399 | 7.30 | 1.00 | 0.48 | 0.013 | 1.31 | 0.96 | 59 | 61 | 39 |
| 7 | 0.256 | 7.35 | 1.56 | 0.64 | 0.011 | 1.32 | 0.62 | 52 | 55 | 45 |
| 8 | 0.206 | 3.37 | 1.94 | 0.34 | 0.011 | 0.61 | 0.50 | 48 | 52 | 48 |
| 9 | 0.134 | 6.73 | 2.99 | 0.90 | 0.009 | 1.21 | 0.32 | 42 | 46 | 54 |
| 10 | 0.089 | 6.32 | 4.49 | 1.09 | 0.008 | 1.13 | 0.22 | 35 | 41 | 59 |
| 11 | 0.056 | 6.71 | 7.12 | 1.55 | 0.007 | 1.20 | 0.14 | 28 | 36 | 64 |
| 12 | 0.037 | 5.12 | 10.87 | 1.54 | 0.006 | 0.92 | 0.09 | 23 | 32 | 68 |
| 13 | 0.024 | 5.41 | 16.83 | 2.11 | 0.005 | 0.97 | 0.06 | 18 | 29 | 71 |
| 14 | 0.015 | 4.96 | 25.83 | 2.46 | 0.005 | 0.89 | 0.04 | 13 | 26 | 74 |
| 15 | 0.012 | 2.40 | 32.21 | 1.34 | 0.004 | 0.43 | 0.03 | 11 | 25 | 75 |
| 16 | 0.010 | 2.17 | 39.70 | 1.36 | 0.004 | 0.39 | 0.02 | 8 | 25 | 75 |
| 17 | 0.008 | 2.15 | 49.45 | 1.50 | 0.004 | 0.39 | 0.02 | 6 | 24 | 76 |
| 18 | 0.007 | 2.24 | 61.45 | 1.72 | 0.003 | 0.40 | 0.02 | 4 | 23 | 77 |
| 19 | 0.005 | 1.69 | 74.94 | 1.35 | 0.003 | 0.30 | 0.01 | 2 | 23 | 77 |
| 20 | 0.004 | 1.50 | 93.78 | 1.20 | 0.003 | 0.27 | 0.01 | 1 | 23 | 77 |
| 21 | 0.004 | 0.84 | 112.55 | 0.67 | 0.003 | 0.15 | 0.01 | 0 | 23 | 77 |

As can be seen from the above, in the method for determining gas saturation of a tight reservoir provided in Example 1, model calculations are used to avoid errors in the determination results of the gas saturation caused by water volatilization, surface adsorption, and observation of water flow during experiments, and also to avoid the effect of repeated rock filling on the pore structure and wettability. This method directly measures at 21 pressure points and directly obtains the gas saturation at multiple pressure points, which is simple and fast. This method can not only determine the single value of total gas saturation, but also give the gas saturation distribution at different pore sizes.

Example 2

In this example, the pore size distribution of a Sandstone 2 sample is determined by NMR, wherein the $T2_i$ relaxation time and the ratio $\lambda i$ are obtained by T2 NMR spectrum measurement, and the pore throat radius is calculated by the formula $r_i = 3 \cdot \rho \cdot T2_i$, where $\rho$ is the rock surface relaxation rate in μm/ms. The results are shown in Table 3.

TABLE 3

The pore size distribution of the Sandstone 2 sample

| No., i | $T2_i$ relaxation time (ms) | $\lambda_i$, % | Pore throat radius $r_i$, μm |
|---|---|---|---|
| 1 | 24.03 | 0.00 | 3.605 |
| 2 | 18.02 | 0.10 | 2.704 |
| 3 | 14.42 | 0.14 | 2.163 |
| 4 | 13.11 | 0.10 | 1.966 |
| 5 | 12.02 | 0.10 | 1.802 |
| 6 | 11.09 | 0.07 | 1.664 |
| 7 | 9.61 | 0.21 | 1.442 |
| 8 | 8.01 | 0.14 | 1.202 |
| 9 | 7.21 | 0.14 | 1.082 |
| 10 | 6.01 | 0.31 | 0.901 |
| 11 | 5.55 | 0.28 | 0.832 |
| 12 | 5.15 | 0.31 | 0.773 |
| 13 | 4.81 | 0.28 | 0.721 |
| 14 | 3.60 | 0.76 | 0.541 |
| 15 | 2.88 | 1.39 | 0.433 |
| 16 | 2.40 | 1.53 | 0.361 |
| 17 | 2.06 | 3.05 | 0.309 |
| 18 | 1.80 | 5.90 | 0.270 |

TABLE 3-continued

The pore size distribution of the Sandstone 2 sample

| No., i | T2$_i$ relaxation time (ms) | $\lambda_i$, % | Pore throat radius $r_i$, μm |
|---|---|---|---|
| 19 | 1.60 | 5.69 | 0.240 |
| 20 | 1.44 | 6.91 | 0.216 |
| 21 | 1.31 | 8.40 | 0.197 |
| 22 | 1.20 | 7.70 | 0.180 |
| 23 | 1.03 | 11.97 | 0.155 |
| 24 | 0.90 | 8.75 | 0.135 |
| 25 | 0.80 | 1.87 | 0.120 |
| 26 | 0.72 | 1.53 | 0.108 |
| 27 | 0.60 | 2.46 | 0.090 |
| 28 | 0.55 | 0.73 | 0.083 |
| 29 | 0.51 | 0.97 | 0.077 |
| 30 | 0.48 | 0.69 | 0.072 |
| 31 | 0.45 | 0.83 | 0.068 |
| 32 | 0.42 | 1.01 | 0.064 |
| 33 | 0.40 | 0.80 | 0.060 |
| 34 | 0.38 | 0.49 | 0.057 |
| 35 | 0.36 | 0.52 | 0.054 |
| 36 | 0.29 | 3.05 | 0.043 |
| 37 | 0.24 | 2.53 | 0.036 |
| 38 | 0.21 | 2.05 | 0.031 |
| 39 | 0.18 | 1.77 | 0.027 |
| 40 | 0.16 | 1.91 | 0.024 |
| 41 | 0.14 | 1.01 | 0.022 |
| 42 | 0.13 | 1.15 | 0.020 |
| 43 | 0.12 | 1.21 | 0.018 |
| 44 | 0.10 | 1.60 | 0.015 |
| 45 | 0.09 | 1.15 | 0.014 |
| 46 | 0.08 | 1.49 | 0.012 |
| 47 | 0.07 | 0.76 | 0.011 |
| 48 | 0.07 | 0.80 | 0.010 |
| 49 | 0.06 | 0.56 | 0.009 |
| 50 | 0.06 | 0.59 | 0.008 |
| 51 | 0.05 | 0.42 | 0.008 |
| 52 | 0.05 | 0.59 | 0.007 |
| 53 | 0.05 | 0.28 | 0.007 |
| 54 | 0.04 | 0.28 | 0.006 |
| 55 | 0.04 | 0.21 | 0.006 |
| 56 | 0.04 | 0.24 | 0.006 |
| 57 | 0.04 | 0.21 | 0.005 |

(1) Free Water Saturation:

The pore size distribution data are converted to the capillary pressure of oil reservoir. The mercury porosimetry curve is converted into the relationship between water saturation and displacement pressure difference, in consideration of the interfacial tension, contact angle, and the like, under the conditions of actual gas reservoir temperature and pressure:

$$P_{filling} = \frac{2\sigma_{gas-water} \cos\theta_{gas-water}}{r}$$

The curve of pore size distribution data and capillary pressure measured in the laboratory is converted into the curve of free water saturation and capillary pressure, to obtain the filling pressure, and thus the free water saturation.

$\sigma_{gas-water}$ is the interfacial tension in mN/m; in this example, the gas-water interfacial tension $\sigma_{gas-water}$=50 mN/m;

$\theta_{gas-water}$ is the gas-water contact angle, $\theta$ is 0, and thus $\cos\theta$=1;

$P_{filling}$ is the gas-water filling pressure in MPa;

r is the capillary radius in $10^{-9}$ m;

(2) Water-Membrane Water Saturation:

The water-membrane thicknesses in the pore spaces corresponding to different pore throat radii is calculated according to the following equation:

$$h_i = \left(\frac{1.18 \times 10^{-4} r_i}{\sigma}\right)^{1/3}$$

wherein $h_i$ is the water-membrane thickness which corresponds to the pore space corresponding to the i-th pore throat radius in μm; σ is the fluid interfacial tension in mN/m; $r_i$ is the pore throat radius which corresponds to the pore space corresponding to the i-th pore throat radius; in this example, i is 1-57, and specific data are shown in Table 1;

the water-membrane saturation is calculated according to the following equation:

$$S_{wmi} = \frac{V_{water film}}{V_{sum}} = \frac{r_i^2 - (r_i - h_i)^2}{r_i^2}$$

wherein $S_{wmi}$ is the water-membrane water saturation of the pore space corresponding to the i-th pore throat radius;

$r_i$ is the pore throat radius which corresponds to the pore space corresponding to the i-th pore throat radius; in this example, i is 1-57, and specific data are shown in Table 1;

$h_i$ is the water-membrane thickness which corresponds to the pore space corresponding to the i-th pore throat radius;

(3) Corner Water Saturation:

The corner water saturation is calculated according to the following equation:

(1) observing the pore structure of the reservoir and directly determining the corner water saturation; this method is suitable for reservoir samples capable of image observation;

(2) according to Table 4, counting the proportions of corner water corresponding to different types of pore structure, and determining the corner water saturation as 28.45 by weighted average;

$S_{wyi}$=31.2×75%+39.57×5%+21.5×10%+9.35×10%=28.45%

TABLE 4

Corner water statistics of the Sandstone 2 sample

| Pore structure | Regular arrangement of spherical particles | Triangular arrangement of spherical particles | Regular triangle pores | Square pores | Regular hexagonal pores |
|---|---|---|---|---|---|
| corner water saturation (%) | 31.2 | 53.34 | 39.57 | 21.5 | 9.35 |
| proportion (%) | 75 | 0 | 5 | 10 | 10 |

(4) Gas Saturation:

The water saturation is calculated according to the following equation:

$$S_w = \sum_{i=1}^{n} \lambda_i (S_{wyi} + S_{wmi}) + \lambda_z S_{wz}$$

wherein $S_w$ is the water saturation;

$\lambda_i$ is the percentage of pore volume occupied by the pore space corresponding to the i-th pore throat radius;

$\lambda_z$ is the proportion of pore volume occupied by free water pore space; $S_{wyi}$ is the corner water saturation in the pore space corresponding to the i-th pore throat radius;

$S_{wmi}$ is the water-membrane water saturation in the pore space corresponding to the i-th pore throat radius;

$S_{wz}$ is the free water saturation, which has not been filled and is 100%.

Figure 5:
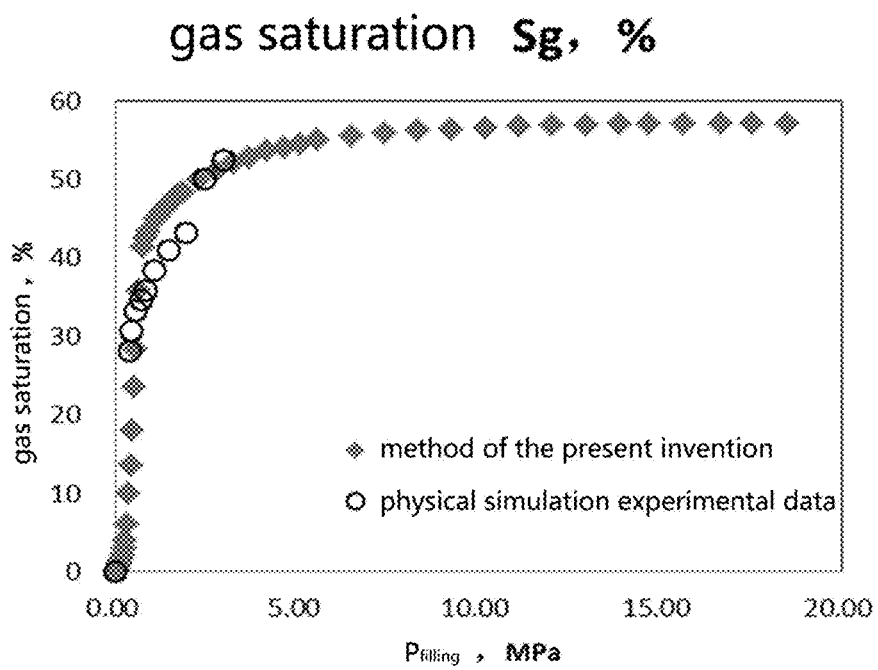
FIG. 5 is a relationship diagram between the filling pressure and the gas saturation in Example 2.
Figure 6:
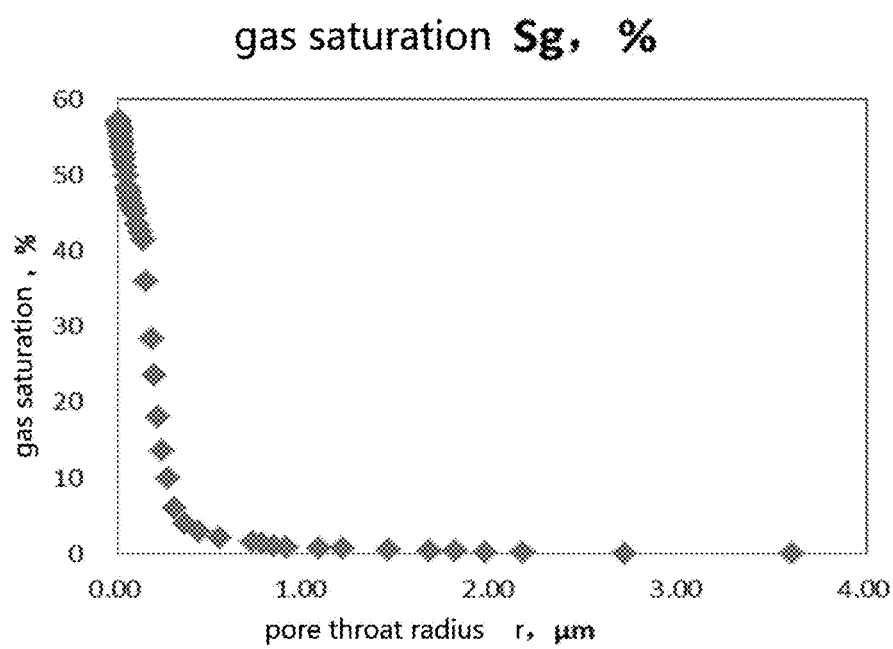
FIG. 6 is a relationship diagram between the filled pore throat radius and the gas saturation in Example 2.

The relationship between the filling pressure and the gas saturation is shown in FIG. 5, and the relationship between the filled pore throat radius and the gas saturation is shown in FIG. 6.

The gas saturation of the tight reservoir rock sample is then calculated according to the following equation:

$$S_g = 100 - S_w$$

wherein $S_w$ is the water saturation in %; the water saturation is the sum of the free water saturation, the water-membrane water saturation and the corner water saturation;

$S_g$ is the gas saturation in %.

The parameters of this example are shown in Table 5, and the physical simulation results corresponding to this example are shown in Table 6.

TABLE 5

Parameters of this example

| No. i | $P_{filling}$ MPa | Swmi % | Water-membrane thickness h, μm | Swyi % | Particle radius R μm | Swz % | Gas saturation Sw % |
|---|---|---|---|---|---|---|---|
| 1 | 0.03 | 0.00 | 0.020 | 0.00 | 8.71 | 100 | 0 |
| 2 | 0.04 | 0.00 | 0.019 | 0.03 | 6.53 | 100 | 0 |
| 3 | 0.05 | 0.00 | 0.017 | 0.04 | 5.22 | 100 | 0 |
| 4 | 0.05 | 0.00 | 0.017 | 0.03 | 4.75 | 100 | 0 |
| 5 | 0.06 | 0.00 | 0.016 | 0.03 | 4.35 | 100 | 0 |
| 6 | 0.06 | 0.00 | 0.016 | 0.02 | 4.02 | 99 | 0 |
| 7 | 0.07 | 0.00 | 0.015 | 0.06 | 3.48 | 99 | 1 |
| 8 | 0.08 | 0.00 | 0.014 | 0.04 | 2.90 | 99 | 1 |
| 9 | 0.09 | 0.00 | 0.014 | 0.04 | 2.61 | 99 | 1 |
| 10 | 0.11 | 0.01 | 0.013 | 0.09 | 2.18 | 99 | 1 |
| 11 | 0.12 | 0.01 | 0.013 | 0.08 | 2.01 | 98 | 1 |
| 12 | 0.13 | 0.01 | 0.012 | 0.09 | 1.87 | 98 | 1 |
| 13 | 0.14 | 0.01 | 0.012 | 0.08 | 1.74 | 98 | 2 |
| 14 | 0.18 | 0.03 | 0.011 | 0.21 | 1.31 | 97 | 2 |
| 15 | 0.23 | 0.06 | 0.010 | 0.39 | 1.04 | 96 | 3 |
| 16 | 0.28 | 0.08 | 0.009 | 0.43 | 0.87 | 94 | 4 |
| 17 | 0.32 | 0.18 | 0.009 | 0.86 | 0.75 | 91 | 6 |
| 18 | 0.37 | 0.37 | 0.009 | 1.65 | 0.65 | 85 | 10 |
| 19 | 0.42 | 0.39 | 0.008 | 1.59 | 0.58 | 79 | 14 |
| 20 | 0.46 | 0.50 | 0.008 | 1.93 | 0.52 | 73 | 18 |
| 21 | 0.51 | 0.65 | 0.008 | 2.35 | 0.47 | 64 | 23 |
| 22 | 0.55 | 0.63 | 0.008 | 2.16 | 0.44 | 56 | 28 |
| 23 | 0.65 | 1.08 | 0.007 | 3.35 | 0.37 | 45 | 36 |
| 24 | 0.74 | 0.86 | 0.007 | 2.45 | 0.33 | 36 | 41 |
| 25 | 0.83 | 0.20 | 0.007 | 0.52 | 0.29 | 34 | 43 |
| 26 | 0.93 | 0.17 | 0.006 | 0.43 | 0.26 | 32 | 43 |
| 27 | 1.11 | 0.32 | 0.006 | 0.69 | 0.22 | 30 | 45 |
| 28 | 1.20 | 0.10 | 0.006 | 0.20 | 0.20 | 29 | 45 |
| 29 | 1.30 | 0.14 | 0.006 | 0.27 | 0.19 | 28 | 46 |
| 30 | 1.39 | 0.10 | 0.006 | 0.19 | 0.17 | 27 | 46 |
| 31 | 1.48 | 0.13 | 0.005 | 0.23 | 0.16 | 27 | 47 |
| 32 | 1.57 | 0.16 | 0.005 | 0.28 | 0.15 | 26 | 47 |
| 33 | 1.66 | 0.13 | 0.005 | 0.22 | 0.15 | 25 | 48 |
| 34 | 1.76 | 0.08 | 0.005 | 0.14 | 0.14 | 24 | 48 |
| 35 | 1.85 | 0.09 | 0.005 | 0.15 | 0.13 | 24 | 48 |
| 36 | 2.31 | 0.62 | 0.005 | 0.86 | 0.10 | 21 | 50 |
| 37 | 2.78 | 0.58 | 0.004 | 0.71 | 0.09 | 18 | 51 |
| 38 | 3.24 | 0.52 | 0.004 | 0.57 | 0.07 | 16 | 52 |
| 39 | 3.70 | 0.48 | 0.004 | 0.50 | 0.07 | 14 | 53 |
| 40 | 4.17 | 0.56 | 0.004 | 0.53 | 0.06 | 13 | 54 |
| 41 | 4.63 | 0.32 | 0.004 | 0.28 | 0.05 | 12 | 54 |
| 42 | 5.08 | 0.38 | 0.004 | 0.32 | 0.05 | 10 | 55 |
| 43 | 5.56 | 0.43 | 0.003 | 0.34 | 0.04 | 9 | 55 |
| 44 | 6.49 | 0.61 | 0.003 | 0.45 | 0.04 | 8 | 56 |
| 45 | 7.41 | 0.47 | 0.003 | 0.32 | 0.03 | 6 | 56 |
| 46 | 8.33 | 0.66 | 0.003 | 0.42 | 0.03 | 5 | 56 |
| 47 | 9.26 | 0.36 | 0.003 | 0.21 | 0.03 | 4 | 56 |
| 48 | 10.20 | 0.40 | 0.003 | 0.22 | 0.02 | 3 | 57 |
| 49 | 11.11 | 0.29 | 0.003 | 0.16 | 0.02 | 3 | 57 |
| 50 | 12.05 | 0.32 | 0.003 | 0.17 | 0.02 | 2 | 57 |
| 51 | 12.99 | 0.24 | 0.003 | 0.12 | 0.02 | 2 | 57 |
| 52 | 13.89 | 0.35 | 0.003 | 0.17 | 0.02 | 1 | 57 |
| 53 | 14.71 | 0.17 | 0.003 | 0.08 | 0.02 | 1 | 57 |
| 54 | 15.63 | 0.17 | 0.002 | 0.08 | 0.02 | 1 | 57 |
| 55 | 16.67 | 0.13 | 0.002 | 0.06 | 0.01 | 0 | 57 |
| 56 | 17.54 | 0.16 | 0.002 | 0.07 | 0.01 | 0 | 57 |

TABLE 5-continued

Parameters of this example

| No. i | $P_{filling}$ MPa | Swmi % | Water-membrane thickness h, μm | Swyi % | Particle radius R μm | Swz % | Gas saturation Sw % |
|---|---|---|---|---|---|---|---|
| 57 | 18.52 | 0.14 | 0.002 | 0.06 | 0.01 | 0 | 57 |

TABLE 6

Physical simulation results corresponding to this example

| $P_{filling}$ MPa | Gas saturation Sw % |
|---|---|
| 0 | 0 |
| 0.4 | 28 |
| 0.45 | 31 |
| 0.57 | 33 |
| 0.73 | 35 |
| 0.83 | 36 |
| 1.06 | 38 |
| 1.46 | 41 |
| 1.95 | 43 |
| 2.46 | 50 |
| 2.97 | 53 |

As can be seen from the above, model calculations are used in the method for determining the gas saturation of a tight reservoir provided in Example 2. As compared with Example 1, the pore throat radius distribution of the sandstone sample was measured by NMR experiments, and the proportion of corner water is obtained by observing the pore type and weighted calculation. In order to verify the validity of the method, it is compared with actual physical simulation experiments. The filling results are consistent with the results calculated by this method, and the physical simulation experimental data is relatively low, because that the experimental time is limited and the actual underground gas reservoir charging time cannot be reached. Therefore, the incomplete charging results in low results. However, because the physical simulation experiment can only reach a lower filling pressure, it can only be verified in the lower filling pressure range, but the above content is sufficient to prove the technical effect of the technical solution of the present invention.

Example 3

The sample in this example is a Sandstone 3 sample having large pores, and the pore size distribution of the Sandstone 3 sample is determined by NMR, wherein the $T2_i$ relaxation time and the ratio $\lambda_i$ are obtained by T2 NMR spectrum measurement, and the pore throat radius is calculated by the equation $r_i = 3 \cdot \rho \cdot T2_i$, where $\rho$ is the rock surface relaxation rate in μm/ms. The results are shown in Table 7.

TABLE 7

The pore size distribution of the Sandstone 3 sample

| NO., i | $T2_i$ relaxation time (ms) | $\lambda_i$, % | Pore throat radius $r_i$, μm |
|---|---|---|---|
| 1 | 10000.00 | 0.00 | 1448.825 |
| 2 | 8697.49 | 0.00 | 1351.653 |
| 3 | 7564.63 | 0.00 | 1260.998 |
| 4 | 6579.33 | 0.00 | 1176.423 |
| 5 | 5722.37 | 0.00 | 1097.521 |
| 6 | 4977.02 | 0.00 | 1023.911 |

TABLE 7-continued

The pore size distribution of the Sandstone 3 sample

| NO., i | $T2_i$ relaxation time (ms) | $\lambda_i$, % | Pore throat radius $r_i$, μm |
|---|---|---|---|
| 7 | 4328.76 | 0.00 | 955.238 |
| 8 | 3764.94 | 0.00 | 891.170 |
| 9 | 3274.55 | 0.00 | 831.400 |
| 10 | 2848.04 | 0.00 | 775.638 |
| 11 | 2477.08 | 0.00 | 723.616 |
| 12 | 2154.43 | 0.00 | 675.084 |
| 13 | 1873.82 | 0.00 | 629.806 |
| 14 | 1629.75 | 0.00 | 587.565 |
| 15 | 1417.47 | 0.00 | 548.157 |
| 16 | 1232.85 | 0.01 | 511.393 |
| 17 | 1072.27 | 0.02 | 477.094 |
| 18 | 932.60 | 0.03 | 445.095 |
| 19 | 811.13 | 0.04 | 415.243 |
| 20 | 705.48 | 0.04 | 387.393 |
| 21 | 613.59 | 0.05 | 361.411 |
| 22 | 533.67 | 0.05 | 337.171 |
| 23 | 464.16 | 0.05 | 314.557 |
| 24 | 403.70 | 0.05 | 293.460 |
| 25 | 351.12 | 0.05 | 273.777 |
| 26 | 305.39 | 0.10 | 255.415 |
| 27 | 265.61 | 0.17 | 238.285 |
| 28 | 231.01 | 0.24 | 222.303 |
| 29 | 200.92 | 0.31 | 207.393 |
| 30 | 174.75 | 0.37 | 193.484 |
| 31 | 151.99 | 0.43 | 180.507 |
| 32 | 132.19 | 0.50 | 168.400 |
| 33 | 114.98 | 0.56 | 157.106 |
| 34 | 100.00 | 0.62 | 146.569 |
| 35 | 86.97 | 0.68 | 136.738 |
| 36 | 75.65 | 0.73 | 127.567 |
| 37 | 65.79 | 0.79 | 119.012 |
| 38 | 57.22 | 0.84 | 111.029 |
| 39 | 49.77 | 0.89 | 103.583 |
| 40 | 43.29 | 0.93 | 96.635 |
| 41 | 37.65 | 0.96 | 90.154 |
| 42 | 32.75 | 0.99 | 84.108 |
| 43 | 28.48 | 1.01 | 78.467 |
| 44 | 24.77 | 1.04 | 73.204 |
| 45 | 21.54 | 1.06 | 68.294 |
| 46 | 18.74 | 1.08 | 63.714 |
| 47 | 16.30 | 1.10 | 59.440 |
| 48 | 14.17 | 1.11 | 55.454 |
| 49 | 12.33 | 1.12 | 51.734 |
| 50 | 10.72 | 1.11 | 48.265 |
| 51 | 9.33 | 1.10 | 45.028 |
| 52 | 8.11 | 1.08 | 42.008 |
| 53 | 7.05 | 1.05 | 39.190 |
| 54 | 6.14 | 1.03 | 36.562 |
| 55 | 5.34 | 1.01 | 34.110 |
| 56 | 4.64 | 1.01 | 31.822 |
| 57 | 4.04 | 1.03 | 29.688 |
| 58 | 3.51 | 1.09 | 27.696 |
| 59 | 3.05 | 1.17 | 25.839 |
| 60 | 2.66 | 1.29 | 24.106 |
| 61 | 2.31 | 1.44 | 22.489 |
| 62 | 2.01 | 1.63 | 20.981 |
| 63 | 1.75 | 1.86 | 19.574 |
| 64 | 1.52 | 2.10 | 18.261 |
| 65 | 1.32 | 2.35 | 17.036 |
| 66 | 1.15 | 2.61 | 15.893 |
| 67 | 1.00 | 2.87 | 14.828 |
| 68 | 0.87 | 3.13 | 13.833 |

TABLE 7-continued

The pore size distribution of the Sandstone 3 sample

| NO., i | T2$_i$ relaxation time (ms) | $\lambda_i$, % | Pore throat radius $r_i$, μm |
|---|---|---|---|
| 69 | 0.76 | 3.35 | 12.905 |
| 70 | 0.66 | 3.55 | 12.040 |
| 71 | 0.57 | 3.71 | 11.232 |
| 72 | 0.50 | 3.83 | 10.479 |
| 73 | 0.43 | 3.90 | 9.776 |
| 74 | 0.38 | 3.91 | 9.120 |
| 75 | 0.33 | 3.85 | 8.509 |
| 76 | 0.28 | 3.73 | 7.938 |
| 77 | 0.25 | 3.54 | 7.406 |
| 78 | 0.22 | 3.30 | 6.909 |
| 79 | 0.19 | 3.02 | 6.446 |
| 80 | 0.16 | 2.68 | 6.013 |
| 81 | 0.14 | 2.32 | 5.610 |
| 82 | 0.12 | 1.94 | 5.234 |
| 83 | 0.11 | 1.57 | 4.883 |
| 84 | 0.09 | 1.22 | 4.555 |
| 85 | 0.08 | 0.91 | 4.250 |
| 86 | 0.07 | 0.65 | 3.965 |
| 87 | 0.06 | 0.44 | 3.699 |
| 88 | 0.05 | 0.27 | 3.451 |
| 89 | 0.05 | 0.16 | 3.219 |
| 90 | 0.04 | 0.09 | 3.003 |
| 91 | 0.04 | 0.04 | 2.802 |
| 92 | 0.03 | 0.02 | 2.614 |
| 93 | 0.03 | 0.01 | 2.439 |
| 94 | 0.02 | 0.00 | 2.275 |
| 95 | 0.02 | 0.00 | 2.123 |
| 96 | 0.02 | 0.00 | 1.980 |
| 97 | 0.02 | 0.00 | 1.847 |
| 98 | 0.01 | 0.00 | 1.724 |
| 99 | 0.01 | 0.00 | 1.608 |
| 100 | 0.01 | 0.00 | 1.500 |

(1) Free Water Saturation:

The pore size distribution data are converted to the capillary pressure of oil reservoir. The mercury porosimetry curve is converted into the relationship between water saturation and displacement pressure difference, in consideration of the interfacial tension, contact angle, and the like, under the conditions of actual gas reservoir temperature and pressure:

$$P_{filling} = \frac{2\sigma_{gas-water} \cos\theta_{gas-water}}{r}$$

The curve of pore size distribution data and capillary pressure measured in the laboratory is converted into the curve of free water saturation and capillary pressure, to obtain the filling pressure, and thus the free water saturation.

$\sigma_{gas-water}$ is the interfacial tension, in mN/m; in this example, the gas-water interfacial tension $\sigma_{gas-water}$=50 mN/m;

$\theta_{gas-water}$ is the gas-water contact angle, $\theta$ is 0, and thus $\cos\theta$=1; $P_{filling}$ is the filling pressure in MPa;

r is the capillary radius in $10^{-9}$ m;

(2) Water-Membrane Water Saturation:

The water-membrane thicknesses in the pore spaces corresponding to different pore throat radii is calculated according to the following equation:

$$h_i = \left(\frac{1.18 \times 10^{-4} r_i}{\sigma}\right)^{1/3}$$

wherein $h_i$ is the water-membrane thickness which corresponds to the pore space corresponding to the i-th pore throat radius in μm; $\sigma$ is the fluid interfacial tension in mN/m; $r_i$ is the pore throat radius which corresponds to the pore space corresponding to the i-th pore throat radius; in this example, i is 1-57, and specific data are shown in Table 1;

the water-membrane saturation is calculated according to the following equation:

$$S_{wmi} = \frac{V_{water-membrane}}{V_{sum}} = \frac{r_i^2 - (r_i - h_i)^2}{r_i^2}$$

wherein $S_{wmi}$ is the water-membrane water saturation of the pore space corresponding to the i-th pore throat radius;

$r_i$ is the pore throat radius which corresponds to the pore space corresponding to the i-th pore throat radius; in this example, i is 1-57, and specific data are shown in Table 1;

$h_i$ is the water-membrane thickness which corresponds to the pore space corresponding to the i-th pore throat radius;

(3) Corner Water Saturation:

The corner water saturation is calculated according to the following equation (see FIG. 2):

$$S_{wyi} = \frac{A_3}{A_2 + A_3} = \frac{4}{4-\pi}\left[\sqrt{\left(\frac{r_i}{R_i}\right)^2 + 2\frac{r_i}{R_i}} - \arccos\left(\frac{R_i}{R_i + r_i}\right) - \left(\frac{r_i}{R_i}\right)^2 \arcsin\left(\frac{R_i}{R_i + r_i}\right)\right]$$

wherein $r_i$ is the arc radius of air-water interface, $$r_i = \frac{2\sigma}{P_{filling\ i}}$$

in $10^{-9}$ m;

$R_i$ is the particle radius of the tight reservoir rock sample in $10^{-9}$ m;

$S_{wyi}$ is the water saturation of the pore space corresponding to the i-th pore throat radius;

$P_{filling\ i}$ is the filling pressure of the pore space corresponding to the i-th pore throat radius in MPa;

$\sigma$ is the fluid interfacial tension in mN/m;

the water saturation is calculated according to the following equation:

$$S_w = \sum_{i=1}^{n} \lambda_i (S_{wyi} + S_{wmi}) + \lambda_z S_{wz}$$

wherein $S_w$ is the water saturation;

$\lambda_i$ is the percentage of pore volume occupied by the pore space corresponding to the i-th pore throat radius;

$\lambda_z$ is the proportion of pore volume occupied by free water pore space;

$S_{wyi}$ is the corner water saturation in the pore space corresponding to the i-th pore throat radius;

$S_{wmi}$ is the water-membrane water saturation in the pore space corresponding to the i-th pore throat radius;

$S_{wz}$ is the free water saturation, which has not been filled and is 100%.

Figure 7:
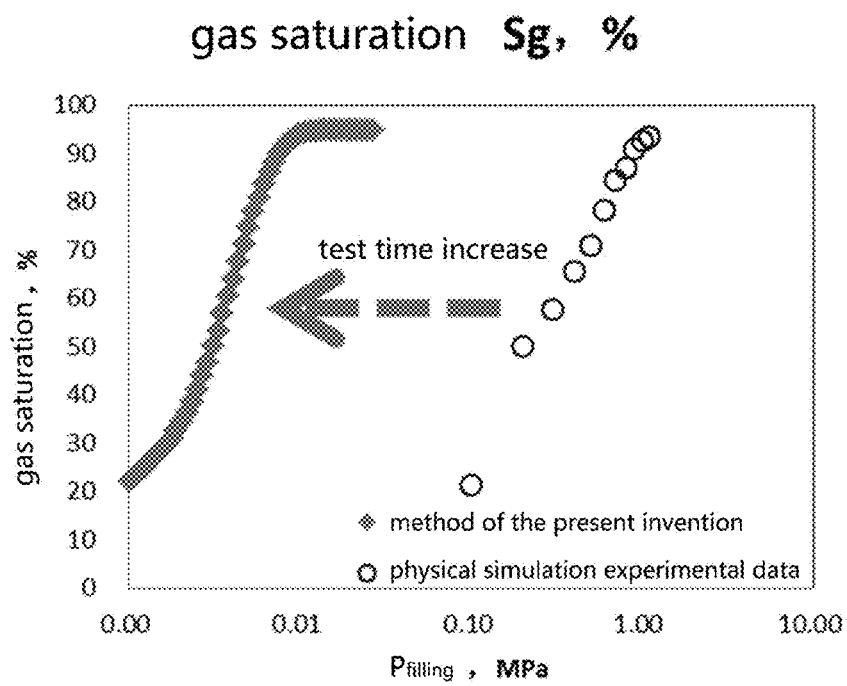
FIG. 7 is a relationship diagram between the filling pressure and the gas saturation in Example 3.
Figure 8:
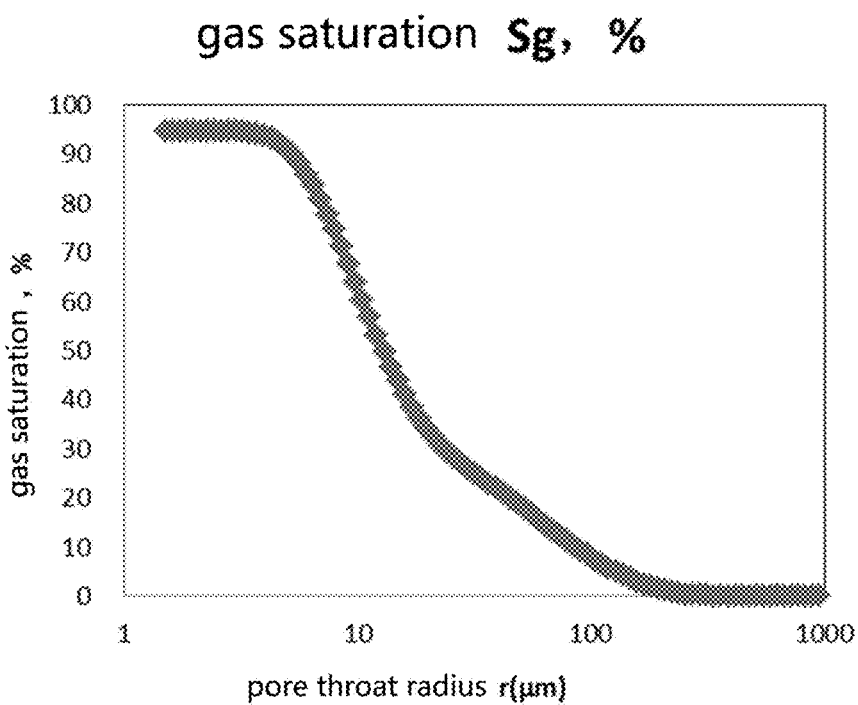
FIG. 8 is a relationship diagram between the filled pore throat radius and the gas saturation in Example 3.

The relationship between the filling pressure and the gas saturation is shown in FIG. 7, and the relationship between the filled pore throat radius and the gas saturation is shown in FIG. 8.

The gas saturation of the tight reservoir rock sample is then calculated according to the following equation:

$$S_g = 100 - S_w$$

wherein $S_w$ is the water saturation in %; the water saturation is the sum of the free water saturation, the water-membrane water saturation and the corner water saturation; $S_g$ is the gas saturation in %.

The parameters of this example are shown in Table 8, and the physical simulation results corresponding to this example are shown in Table 9.

TABLE 8

Parameters of this example

| No. i | pore throat radius $r_i$ μm | $\lambda_i$ % | $P_{filling}$ MPa | Swmi % | Water-membrane thickness $h_i$ μm | Swyi % | Particle radius R μm | Swz % | Water saturation Sw % |
|---|---|---|---|---|---|---|---|---|---|
| 1 | 1448.825 | 0.00 | 0.00 | 0.00 | 0.204 | 0.00 | 3499.58 | 100 | 0 |
| 2 | 1351.653 | 0.00 | 0.00 | 0.00 | 0.200 | 0.00 | 3264.86 | 100 | 0 |
| 3 | 1260.998 | 0.00 | 0.00 | 0.00 | 0.195 | 0.00 | 3045.89 | 100 | 0 |
| 4 | 1176.423 | 0.00 | 0.00 | 0.00 | 0.191 | 0.00 | 2841.60 | 100 | 0 |
| 5 | 1097.521 | 0.00 | 0.00 | 0.00 | 0.186 | 0.00 | 2651.02 | 100 | 0 |
| 6 | 1023.911 | 0.00 | 0.00 | 0.00 | 0.182 | 0.00 | 2473.21 | 100 | 0 |
| 7 | 955.238 | 0.00 | 0.00 | 0.00 | 0.178 | 0.00 | 2307.34 | 100 | 0 |
| 8 | 891.170 | 0.00 | 0.00 | 0.00 | 0.174 | 0.00 | 2152.58 | 100 | 0 |
| 9 | 831.400 | 0.00 | 0.00 | 0.00 | 0.170 | 0.00 | 2008.21 | 100 | 0 |
| 10 | 775.638 | 0.00 | 0.00 | 0.00 | 0.166 | 0.00 | 1873.52 | 100 | 0 |
| 11 | 723.616 | 0.00 | 0.00 | 0.00 | 0.162 | 0.00 | 1747.87 | 100 | 0 |
| 12 | 675.084 | 0.00 | 0.00 | 0.00 | 0.159 | 0.00 | 1630.64 | 100 | 0 |
| 13 | 629.806 | 0.00 | 0.00 | 0.00 | 0.155 | 0.00 | 1521.27 | 100 | 0 |
| 14 | 587.565 | 0.00 | 0.00 | 0.00 | 0.151 | 0.00 | 1419.24 | 100 | 0 |
| 15 | 548.157 | 0.00 | 0.00 | 0.00 | 0.148 | 0.00 | 1324.05 | 100 | 0 |
| 16 | 511.393 | 0.01 | 0.00 | 0.00 | 0.145 | 0.00 | 1235.25 | 100 | 0 |
| 17 | 477.094 | 0.02 | 0.00 | 0.00 | 0.141 | 0.00 | 1152.40 | 100 | 0 |
| 18 | 445.095 | 0.03 | 0.00 | 0.00 | 0.138 | 0.01 | 1075.11 | 100 | 0 |
| 19 | 415.243 | 0.04 | 0.00 | 0.00 | 0.135 | 0.00 | 1003.00 | 100 | 0 |
| 20 | 387.393 | 0.04 | 0.00 | 0.00 | 0.132 | 0.01 | 935.73 | 100 | 0 |
| 21 | 361.411 | 0.05 | 0.00 | 0.00 | 0.129 | 0.00 | 872.97 | 100 | 0 |
| 22 | 337.171 | 0.05 | 0.00 | 0.00 | 0.126 | 0.01 | 814.42 | 100 | 0 |
| 23 | 314.557 | 0.05 | 0.00 | 0.00 | 0.123 | 0.00 | 759.80 | 100 | 0 |
| 24 | 293.460 | 0.05 | 0.00 | 0.00 | 0.120 | 0.01 | 708.84 | 100 | 0 |
| 25 | 273.777 | 0.05 | 0.00 | 0.00 | 0.117 | 0.00 | 661.30 | 100 | 0 |
| 26 | 255.415 | 0.10 | 0.00 | 0.00 | 0.115 | 0.02 | 616.95 | 100 | 0 |
| 27 | 238.285 | 0.17 | 0.00 | 0.00 | 0.112 | 0.00 | 575.57 | 99 | 1 |
| 28 | 222.303 | 0.24 | 0.00 | 0.00 | 0.109 | 0.04 | 536.96 | 99 | 1 |
| 29 | 207.393 | 0.31 | 0.00 | 0.00 | 0.107 | 0.00 | 500.95 | 99 | 1 |
| 30 | 193.484 | 0.37 | 0.00 | 0.00 | 0.105 | 0.07 | 467.35 | 98 | 2 |
| 31 | 180.507 | 0.43 | 0.00 | 0.00 | 0.102 | 0.00 | 436.01 | 98 | 2 |
| 32 | 168.400 | 0.50 | 0.00 | 0.00 | 0.100 | 0.09 | 406.76 | 97 | 2 |
| 33 | 157.106 | 0.56 | 0.00 | 0.00 | 0.098 | 0.00 | 379.48 | 97 | 3 |
| 34 | 146.569 | 0.62 | 0.00 | 0.00 | 0.095 | 0.11 | 354.03 | 96 | 4 |
| 35 | 136.738 | 0.68 | 0.00 | 0.00 | 0.093 | 0.00 | 330.29 | 96 | 4 |
| 36 | 127.567 | 0.73 | 0.00 | 0.00 | 0.091 | 0.13 | 308.13 | 95 | 5 |
| 37 | 119.012 | 0.79 | 0.00 | 0.00 | 0.089 | 0.00 | 287.47 | 94 | 6 |
| 38 | 111.029 | 0.84 | 0.00 | 0.00 | 0.087 | 0.15 | 268.19 | 93 | 7 |
| 39 | 103.583 | 0.89 | 0.00 | 0.00 | 0.085 | 0.00 | 250.20 | 92 | 8 |
| 40 | 96.635 | 0.93 | 0.00 | 0.00 | 0.083 | 0.17 | 233.42 | 91 | 8 |
| 41 | 90.154 | 0.96 | 0.00 | 0.00 | 0.081 | 0.00 | 217.76 | 91 | 9 |
| 42 | 84.108 | 0.99 | 0.00 | 0.00 | 0.079 | 0.18 | 203.16 | 90 | 10 |
| 43 | 78.467 | 1.01 | 0.00 | 0.00 | 0.077 | 0.00 | 189.53 | 89 | 11 |
| 44 | 73.204 | 1.04 | 0.00 | 0.00 | 0.076 | 0.19 | 176.82 | 87 | 12 |
| 45 | 68.294 | 1.06 | 0.00 | 0.00 | 0.074 | 0.00 | 164.96 | 86 | 13 |
| 46 | 63.714 | 1.08 | 0.00 | 0.00 | 0.072 | 0.19 | 153.90 | 85 | 15 |
| 47 | 59.440 | 1.10 | 0.00 | 0.00 | 0.071 | 0.00 | 143.58 | 84 | 16 |
| 48 | 55.454 | 1.11 | 0.00 | 0.00 | 0.069 | 0.20 | 133.95 | 83 | 17 |
| 49 | 51.734 | 1.12 | 0.00 | 0.00 | 0.067 | 0.00 | 124.96 | 82 | 18 |
| 50 | 48.265 | 1.11 | 0.00 | 0.00 | 0.066 | 0.20 | 116.58 | 81 | 19 |
| 51 | 45.028 | 1.10 | 0.00 | 0.00 | 0.064 | 0.00 | 108.76 | 80 | 20 |
| 52 | 42.008 | 1.08 | 0.00 | 0.00 | 0.063 | 0.19 | 101.47 | 79 | 21 |
| 53 | 39.190 | 1.05 | 0.00 | 0.00 | 0.061 | 0.00 | 94.66 | 78 | 22 |
| 54 | 36.562 | 1.03 | 0.00 | 0.00 | 0.060 | 0.19 | 88.31 | 77 | 23 |
| 55 | 34.110 | 1.01 | 0.00 | 0.00 | 0.059 | 0.00 | 82.39 | 76 | 24 |
| 56 | 31.822 | 1.01 | 0.00 | 0.00 | 0.057 | 0.18 | 76.86 | 75 | 25 |
| 57 | 29.688 | 1.03 | 0.00 | 0.00 | 0.056 | 0.00 | 71.71 | 74 | 26 |
| 58 | 27.696 | 1.09 | 0.00 | 0.00 | 0.055 | 0.20 | 66.90 | 72 | 27 |
| 59 | 25.839 | 1.17 | 0.00 | 0.00 | 0.053 | 0.00 | 62.41 | 71 | 28 |
| 60 | 24.106 | 1.29 | 0.00 | 0.01 | 0.052 | 0.23 | 58.23 | 70 | 29 |
| 61 | 22.489 | 1.44 | 0.00 | 0.01 | 0.051 | 0.00 | 54.32 | 69 | 31 |
| 62 | 20.981 | 1.63 | 0.00 | 0.01 | 0.050 | 0.29 | 50.68 | 67 | 32 |
| 63 | 19.574 | 1.86 | 0.00 | 0.01 | 0.049 | 0.00 | 47.28 | 65 | 34 |

TABLE 8-continued

Parameters of this example

| No. i | pore throat radius $r_i$ μm | $\lambda_i$ % | $P_{filling}$ MPa | Swmi % | Water-membrane thickness h, μm | Swyi % | Particle radius R μm | Swz % | Water saturation Sw % |
|---|---|---|---|---|---|---|---|---|---|
| 64 | 18.261 | 2.10 | 0.00 | 0.01 | 0.048 | 0.38 | 44.11 | 63 | 36 |
| 65 | 17.036 | 2.35 | 0.00 | 0.01 | 0.046 | 0.00 | 41.15 | 61 | 39 |
| 66 | 15.893 | 2.61 | 0.00 | 0.01 | 0.045 | 0.47 | 38.39 | 58 | 41 |
| 67 | 14.828 | 2.87 | 0.00 | 0.02 | 0.044 | 0.00 | 35.82 | 55 | 44 |
| 68 | 13.833 | 3.13 | 0.00 | 0.02 | 0.043 | 0.56 | 33.41 | 52 | 47 |
| 69 | 12.905 | 3.35 | 0.00 | 0.02 | 0.042 | 0.00 | 31.17 | 49 | 50 |
| 70 | 12.040 | 3.55 | 0.00 | 0.02 | 0.041 | 0.64 | 29.08 | 45 | 53 |
| 71 | 11.232 | 3.71 | 0.00 | 0.03 | 0.040 | 0.00 | 27.13 | 41 | 57 |
| 72 | 10.479 | 3.83 | 0.00 | 0.03 | 0.040 | 0.69 | 25.31 | 38 | 60 |
| 73 | 9.776 | 3.90 | 0.00 | 0.03 | 0.039 | 0.00 | 23.61 | 34 | 64 |
| 74 | 9.120 | 3.91 | 0.00 | 0.03 | 0.038 | 0.70 | 22.03 | 30 | 68 |
| 75 | 8.509 | 3.85 | 0.00 | 0.03 | 0.037 | 0.00 | 20.55 | 26 | 71 |
| 76 | 7.938 | 3.73 | 0.01 | 0.03 | 0.036 | 0.67 | 19.17 | 22 | 75 |
| 77 | 7.406 | 3.54 | 0.01 | 0.03 | 0.035 | 0.00 | 17.89 | 19 | 78 |
| 78 | 6.909 | 3.30 | 0.01 | 0.03 | 0.034 | 0.59 | 16.69 | 15 | 81 |
| 79 | 6.446 | 3.02 | 0.01 | 0.03 | 0.034 | 0.00 | 15.57 | 12 | 84 |
| 80 | 6.013 | 2.68 | 0.01 | 0.03 | 0.033 | 0.48 | 14.52 | 10 | 86 |
| 81 | 5.610 | 2.32 | 0.01 | 0.03 | 0.032 | 0.00 | 13.55 | 7 | 88 |
| 82 | 5.234 | 1.94 | 0.01 | 0.02 | 0.031 | 0.35 | 12.64 | 5 | 90 |
| 83 | 4.883 | 1.57 | 0.01 | 0.02 | 0.031 | 0.00 | 11.79 | 4 | 91 |
| 84 | 4.555 | 1.22 | 0.01 | 0.02 | 0.030 | 0.22 | 11.00 | 3 | 92 |
| 85 | 4.250 | 0.91 | 0.01 | 0.01 | 0.029 | 0.00 | 10.26 | 2 | 93 |
| 86 | 3.965 | 0.65 | 0.01 | 0.01 | 0.029 | 0.12 | 9.58 | 1 | 94 |
| 87 | 3.699 | 0.44 | 0.01 | 0.01 | 0.028 | 0.00 | 8.93 | 1 | 94 |
| 88 | 3.451 | 0.27 | 0.01 | 0.00 | 0.027 | 0.05 | 8.33 | 0 | 94 |
| 89 | 3.219 | 0.16 | 0.01 | 0.00 | 0.027 | 0.00 | 7.78 | 0 | 95 |
| 90 | 3.003 | 0.09 | 0.01 | 0.00 | 0.026 | 0.02 | 7.25 | 0 | 95 |
| 91 | 2.802 | 0.04 | 0.01 | 0.00 | 0.025 | 0.00 | 6.77 | 0 | 95 |
| 92 | 2.614 | 0.02 | 0.02 | 0.00 | 0.025 | 0.00 | 6.31 | 0 | 95 |
| 93 | 2.439 | 0.01 | 0.02 | 0.00 | 0.024 | 0.00 | 5.89 | 0 | 95 |
| 94 | 2.275 | 0.00 | 0.02 | 0.00 | 0.024 | 0.00 | 5.50 | 0 | 95 |
| 95 | 2.123 | 0.00 | 0.02 | 0.00 | 0.023 | 0.00 | 5.13 | 0 | 95 |
| 96 | 1.980 | 0.00 | 0.02 | 0.00 | 0.023 | 0.00 | 4.78 | 0 | 95 |
| 97 | 1.847 | 0.00 | 0.02 | 0.00 | 0.022 | 0.00 | 4.46 | 0 | 95 |
| 98 | 1.724 | 0.00 | 0.02 | 0.00 | 0.022 | 0.00 | 4.16 | 0 | 95 |
| 99 | 1.608 | 0.00 | 0.02 | 0.00 | 0.021 | 0.00 | 3.88 | 0 | 95 |
| 100 | 1.500 | 0.00 | 0.03 | 0.00 | 0.021 | 0.00 | 3.62 | 0 | 95 |

TABLE 9

Physical simulation results corresponding to this example

| $P_{filling}$ MPa | Gas saturation Sw % |
|---|---|
| 0.1 | 21.41 |
| 0.2 | 50.12 |
| 0.3 | 57.54 |
| 0.4 | 65.46 |
| 0.5 | 70.96 |
| 0.6 | 78.24 |
| 0.7 | 84.50 |
| 0.8 | 86.98 |
| 0.9 | 90.94 |
| 1 | 92.51 |
| 1.1 | 93.37 |

As can be seen from FIG. 8, model calculations are used in the method for determining the gas saturation of a tight reservoir having large pores provided in Example 3, and compared with the physical simulation experiments. As compared with the actual physical simulation experiments, it is found that the final gas saturation data are consistent, but the experimental results at different pressure points are significantly different from those calculated by this method. The reason is analyzed to be that: when reaching a certain gas saturation condition, since the rock sample has large pores, the method of the present invention only needs to give a small pressure and can be completed in an infinite time in a gas reservoir; however, when reaching the same gas saturation condition, it is not easy to set a pressure of less than 0.01 MPa in the physical simulation experiment instrument, and it can only set a higher pressure than the method of the present invention. The consistency between the final gas saturation data demonstrates the accuracy of the method of the present invention from a certain aspect. Moreover, the method of the present invention has reached the low-pressure condition that is not easily reached by the physical simulation experimental instruments at present, which proves the technical advantages of the technical solution of the present invention.

What is claimed is:

1. A method for determining the gas saturation of a tight reservoir, comprising:
   a free water saturation calculation step: determining the pore size distribution of the tight reservoir rock sample, and calculating the free water saturation of the tight reservoir rock sample from the pore size distribution, wherein in the free water saturation calculation step, the pore size distribution of the tight reservoir rock sample is determined by mercury porosimetry as follows:
   injecting mercury into rock pores to displace air in rock pores;
   when the injection pressure exceeds the capillary pressure, mercury entering the pore throat of the rock sample, and at this time, the injection pressure being the capillary pressure, the capillary radius corresponding to the pressure is equivalent to the pore throat radius, and the volume of mercury entering the pores being the pore volume;

increasing the injection pressure such that mercury enters the pores controlled by a smaller throat, to obtain the pore throat radius and the pore volume corresponding to the smaller throat; and repeatedly increasing the injection pressure to obtain the pore throat radii and the pore volumes corresponding to different throats;

a water-membrane water saturation calculation step: calculating the water-membrane water saturation of the tight reservoir rock sample;

a corner water saturation calculation step: calculating the corner water saturation of the tight reservoir rock sample; and a gas saturation calculation step: calculating the gas saturation of the tight reservoir rock sample according to the following equation:

$$S_g = 100 - S_w$$

wherein $S_w$ is the water saturation in %; the water saturation is the sum of the free water saturation, the water-membrane water saturation and the corner water saturation; and wherein $S_g$ is the gas saturation in %.

2. The method according to claim 1, wherein in the free water saturation calculation step, the data of the pore size distribution includes data of pore spaces corresponding to different pore throat radii.

3. The method according to claim 2, wherein in the free water saturation calculation step, the data of pore spaces corresponding to different pore throat radii includes the pore throat radii corresponding to the pore spaces with different radii and the percentages of pore volume occupied by the pore spaces with different radii.

4. The method according to claim 1, wherein in the free water saturation calculation step, the free water saturation of the tight reservoir rock sample is calculated from the pore size distribution as follows:

(1) obtaining the relationship between the injection pressure and the pore volume from the pore throat radii and the pore volumes corresponding to different throats in the tight reservoir rock sample;

$$P_{mercury-air} = \frac{2\sigma_{mercury-air} \cos\theta_{mercury-air}}{r}$$

wherein $P_{mercury-air}$ is the capillary pressure in $10^6$ Pa; $\sigma_{mercury-air}$ is the fluid interfacial tension between mercury and air in mN/m; $\theta_{mercury-air}$ is the wet contact angle between mercury and air in °; r is the capillary radius in $10^{-9}$ m; in the mercury porosimetry, $\sigma_{mercury-air}=480$ mN/m, $\theta_{mercury-air}=140°$;

(2) converting the laboratory pore-throat distribution data into gas-water filling pressure $P_{gas-water}$ under the conditions of oil reservoir, in consideration of the interfacial tension, contact angle, and the like under the conditions of actual gas reservoir temperature and pressure:

$$P_{filling} = \frac{2\sigma_{gas-water} \cos\theta_{gas-water}}{r}$$

$\sigma_{gas-water}$ is the interfacial tension in mN/m; preferably, the gas-water interfacial tension $\sigma_{gas-water}=20$ mN/m;

$\theta_{gas-water}$ is the gas-water contact angle; preferably, $\theta$ is 0, and $\cos\theta=1$;

$P_{filling}$ is the gas-water filling pressure in MPa;

r is the capillary radius in $10^{-9}$ m;

(3) converting the curve of the pore size distribution of different pore throat radius ranges and the capillary pressure into the relationship curve of free water saturation and capillary pressure; obtaining the free water saturation from the filling pressure, that is, calculating the corresponding pore throat radius from the filling pressure, and summing the pore volumes larger than this radius, the percentage of this sum to the total pore volumes being the free water saturation.

5. The method according to claim 1, wherein the water-membrane water saturation calculation step is performed as follows:

(1) calculating the water-membrane thicknesses in the pore spaces corresponding to different pore throat radii according to the following equation:

$$h = \left(\frac{a \cdot r}{\sigma}\right)^{1/3}$$

wherein a is a constant; the more hydrophilic the reservoir is, the greater is its value, which is preferably $1.18 \times 10^{-7}$; h is the water-membrane thickness in μm; σ is the fluid interfacial tension in mN/m; r is the pore throat radius in $10^{-9}$ m;

(2) calculating the water-membrane saturation according to the following equation:

$$S_{wmi} = \frac{V_{water-membrane}}{V_{sum}} = \frac{r^2 - (r-h)^2}{r^2}$$

wherein $S_{wmi}$ is water-membrane water saturation of the pore space corresponding to the i-th pore throat radius;

r is the pore throat radius which corresponds to the pore space corresponding to the i-th pore throat radius;

h is the water-membrane thickness which corresponds to the pore space corresponding to the i-th pore throat radius.

6. The method according to claim 1, wherein the corner water saturation calculation step is performed by one of:

(1) observing the pore structure of the reservoir and directly determining the corner water saturation;

(2) counting the proportions of corner water corresponding to different types of pore structure, and determining the corner water saturation by weighted average;

(3) calculating the corner water saturation according to the following equation:

$$S_{wyi} = \frac{A_3}{A_2 + A_3} = \frac{4}{4-\pi}\left[\sqrt{\left(\frac{r}{R}\right)^2 + 2\frac{r}{R}} - \arccos\left(\frac{R}{R+r}\right) - \left(\frac{r}{R}\right)^2 \arcsin\left(\frac{R}{R+r}\right)\right]$$

wherein r is the arc radius of air-water interface, that is, the pore throat radius, $$r = \frac{2\sigma}{p_{filling}}$$

in $10^{-9}$ m;

R is the particle radius of the tight reservoir rock sample in $10^{-9}$ m;
$S_{wyi}$ is the water saturation of the pore space corresponding to the i-th pore throat radius;
$P_{filling}$ is the filling pressure in MPa;
σ is the fluid interfacial tension in mN/m.

7. The method according to claim 1, wherein the gas saturation calculation step is performed as follows:
  (1) calculating the water saturation according to the following equation:

$$S_w = \sum_{i=1}^{n} \lambda_i (S_{wyi} + S_{wmi}) + S_{wz}$$

wherein $S_w$ is the water saturation;
$\lambda_i$ is the percentage of pore volume occupied by the pore space corresponding to the i-th pore throat radius;
$S_{wyi}$ is the corner water saturation in the pore space corresponding to the i-th pore throat radius;
$S_{wmi}$ is the water-membrane water saturation in the pore space corresponding to the i-th pore throat radius;
$S_{wz}$ is the free water saturation, that is, the proportion of pore volume occupied by free water pore space;
  (2) calculating the gas saturation of the tight reservoir rock sample according to the following equation:

$$S_g = 100 - S_w$$

wherein $S_w$ is the water saturation in %; the water saturation is the sum of the free water saturation, the water-membrane water saturation and the corner water saturation;
$S_g$ is the gas saturation in %.

8. The method according to claim 1, comprising:
a free water saturation calculation step:
determining the pore size distribution of the tight reservoir rock sample by mercury porosimetry; when the injection pressure exceeds the capillary pressure, mercury entering the pore throat of the rock sample, and at this time, the injection pressure being the capillary pressure, the capillary radius corresponding to the capillary pressure being equivalent to the pore throat radius, and the volume of mercury entering the pores being the pore volume;
increasing the injection pressure such that mercury enters the pores controlled by a smaller throat, to obtain the corresponding pore throat radius and pore volume;
continuously increasing the injection pressure to obtain the relationship between the injection pressure, that is, the capillary pressure, and the pore volume;
calculating the gas saturation from the volume of mercury injected and the pore volume of the tight reservoir rock sample, and then obtaining the curve of the pore size distribution of different pore throat radius ranges and the capillary pressure;
converting the pore size distribution data of the tight reservoir rock sample into the capillary pressure of oil reservoir; and converting the mercury porosimetry curve into the relationship of water saturation according to the displacement pressure difference, in consideration of the interfacial tension and the contact angle under the conditions of actual gas reservoir temperature and pressure, $$P_{filling} = \frac{2\sigma_{gas-water} \cos\theta_{gas-water}}{r}$$

converting the curve of pore size distribution data and capillary pressure of the tight reservoir rock sample into the curve of free water saturation and capillary pressure, to obtain the filling pressure, so as to obtain the free water saturation; that is, calculating the corresponding pore throat radius from the filling pressure, and summing the pore volumes larger than this radius, the percentage of this sum to the total pore volumes being the free water saturation; $\sigma_{gas-water}$ is the interfacial tension in mN/m; preferably, the gas-water interfacial tension $\sigma_{gas-water}$=20 mN/m;
$\theta_{gas-water}$ is the gas-water contact angle; preferably, θ is 0, and cos θ=1;
$P_{filling}$ is the filling pressure in MPa;
r is the capillary radius in $10^{-9}$ m;
a water-membrane water saturation calculation step:
calculating the water-membrane thicknesses in the pore spaces corresponding to different pore throat radii according to the following equation:

$$h = \left(\frac{a \cdot r}{\sigma}\right)^{1/3}$$

wherein a is a constant; the more hydrophilic the reservoir is, the greater is its value, which is preferably 1.18× $10^{-7}$; h is the water-membrane thickness in μm; σ is the fluid interfacial tension in mN/m; r is the pore throat radius in $10^{-9}$ m;
calculating the water-membrane saturation according to the following equation:

$$S_{wmi} = \frac{V_{water-membrane}}{V_{sum}} = \frac{r^2 - (r-h)^2}{r^2}$$

wherein $S_{wmi}$ is the water-membrane water saturation of the pore space corresponding to the i-th pore throat radius;
r is the pore throat radius which corresponds to the pore space corresponding to the i-th pore throat radius;
h is the water-membrane thickness which corresponds to the pore space corresponding to the i-th pore throat radius;
a corner water saturation calculation step:
calculating the corner water saturation according to the following equation:

$$S_{wyi} = \frac{A_3}{A_2 + A_3} = \frac{4}{4-\pi}\left[\sqrt{\left(\frac{r}{R}\right)^2 + 2\frac{r}{R}} - \arccos\left(\frac{R}{R+r}\right) - \left(\frac{r}{R}\right)^2 \arcsin\left(\frac{R}{R+r}\right)\right]$$

wherein r is the arc radius of air-water interface, that is, the pore throat radius, $$r = \frac{2\sigma}{p_{filling}}$$

in $10^{-9}$ m;

R is the particle radius of the tight reservoir rock sample in $10^{-9}$ m;

$S_{wyi}$ is the water saturation of the pore space corresponding to the i-th pore throat radius;

$P_{filling}$ is the filling pressure in MPa;

$\sigma$ is the fluid interfacial tension in mN/m;

a gas saturation calculation step:

calculating the water saturation according to the following equation:

$$S_w = \sum_{i=1}^{n} \lambda_i (S_{wyi} + S_{wmi}) + S_{wz}$$

wherein $S_w$ is the water saturation;

$\lambda_i$ is the percentage of pore volume occupied by the pore space corresponding to the i-th pore throat radius;

$S_{wyi}$ is the corner water saturation in the pore space corresponding to the i-th pore throat radius;

$S_{wmi}$ is the water-membrane water saturation in the pore space corresponding to the i-th pore throat radius;

$S_{wz}$ is the free water saturation, that is, the proportion of pore volume occupied by the free water pore space;

then calculating the gas saturation of the tight reservoir rock sample according to the following equation:

$$S_g = 100 - S_w$$

wherein $S_w$ is the water saturation in %; the water saturation is the sum of the free water saturation, the water-membrane water saturation and the corner water saturation;

$S_g$ is the gas saturation in %.

9. The method according to claim 1, wherein the method is based on the following premises:

assuming that the reservoir rock contains only two fluids, formation water and natural gas, and the gas saturation is directly affected by the rock water saturation; if the reservoir water saturation is obtained, the gas saturation can be obtained;

the size and stacking relationship of the rock-forming mineral particles determine the geometry and spatial distribution of the fluid storage space;

the formation water exists in rocks in three main forms:

(1) free water: pore water that cannot be expelled by natural gas, occupying small pore throats that cannot be filled, and its saturation is affected by natural gas filling pressure and pore throat capillary force;

(2) water-membrane water: adsorbed on the pore wall in the form of a thin membrane, its saturation is related to the surface area of the pore wall and the thickness of the water-membrane;

(3) corner water: existing in the corners that are difficult to displace among the particles, and its saturation is affected by the size and the contact relationship of the rock particles.

* * * * *

UNITED STATES PATENT AND TRADEMARK OFFICE
CERTIFICATE OF CORRECTION

PATENT NO. : 11,268,944 B2
APPLICATION NO. : 16/776773
DATED : March 8, 2022
INVENTOR(S) : Tian et al.

Page 1 of 1

It is certified that error appears in the above-identified patent and that said Letters Patent is hereby corrected as shown below:

In the Claims

Column 26, Line 31, remove "his the water-membrane" and insert --h is the water-membrane--

Signed and Sealed this
Twenty-sixth Day of April, 2022

*Katherine Kelly Vidal*

Katherine Kelly Vidal
*Director of the United States Patent and Trademark Office*